US008552057B2

(12) United States Patent
Brinton et al.

(10) Patent No.: US 8,552,057 B2
(45) Date of Patent: *Oct. 8, 2013

(54) PHYTOESTROGENIC FORMULATIONS FOR ALLEVIATION OR PREVENTION OF NEURODEGENERATIVE DISEASES

(75) Inventors: Roberta Diaz Brinton, Rancho Palos Verdes, CA (US); Liqin Zhao, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/362,825

(22) Filed: Jan. 31, 2012

(65) Prior Publication Data
US 2012/0164122 A1 Jun. 28, 2012

Related U.S. Application Data

(62) Division of application No. 11/777,951, filed on Jul. 13, 2007.

(60) Provisional application No. 60/819,849, filed on Aug. 2, 2006, provisional application No. 60/889,920, filed on Feb. 14, 2007, provisional application No. 60/943,190, filed on Jun. 11, 2007.

(51) Int. Cl.
A61K 31/35 (2006.01)

(52) U.S. Cl.
USPC ........................................................ 514/454

(58) Field of Classification Search
USPC ........................................................ 514/454
See application file for complete search history.

(56) References Cited

U.S. PATENT DOCUMENTS

| | | | |
|---|---|---|---|
| 5,952,374 | A | 9/1999 | Clarkson |
| 6,335,038 | B1 | 1/2002 | Cavazza |
| 2002/0001565 | A1 | 1/2002 | Shapiro |
| 2004/0072765 | A1 | 4/2004 | Kelly |
| 2004/0106561 | A1 | 6/2004 | Kelly |
| 2005/0004360 | A1 | 1/2005 | Gayo-Fung et al. |
| 2005/0058709 | A1 | 3/2005 | Fisher |
| 2005/0245492 | A1 | 11/2005 | Lephart |
| 2008/0108696 | A1 | 5/2008 | Brinton et al. |

FOREIGN PATENT DOCUMENTS

| | | |
|---|---|---|
| EP | 0149551 | 7/1985 |
| JP | 2001523258 | 11/2001 |
| JP | 2002542286 | 11/2002 |
| JP | 2006504409 | 2/2006 |
| WO | 9423716 | 10/1994 |
| WO | 9850026 | 11/1998 |
| WO | 0064438 | 11/2000 |
| WO | 02051821 | 7/2002 |
| WO | 2004009035 | 1/2004 |
| WO | 2005089567 | 9/2005 |

OTHER PUBLICATIONS

Morito et al. Interaction of Phytoestrogens with Estrogen Receptors a and b (II). Biol. Pharm. Bull. 25(1), pp. 48-52 (2002).*
Kinjo et al. Interactions of Phytoestrogens with Estrogen Receptors a and b (III). Biol. Pharm. Bull. 27(2) pp. 185-188 (2004).*
An, et al., "Estrogen receptor $^2$-selective transcriptional activity and recruitment of coregulators by phytoestrogens", J Biol. Chem., 276(21):17808-14 (2001).
Avis, et al, 'Is there a menopausal syndrome? Menopausal status and symptoms across racial/ethnic groups', Soc. Sci. Med., 52(3):345-56 (2001).
Brinton, et al, 'Impact of estrogen therapy on Alzheimer's disease: a fork in the road?' CNS Drugs, 18(7):405-422 (2004).
Bromberger, et al, 'Psychologic distress and natural menopause: a multiethnic community study', Am. J. Public Health, 91(9)1435-42 (2001).
Brookmeyer, et al., "Projections of Alzheimer's disease in the United States and the public health impact of delaying disease onset", Am. J. Public Health, 88(9):1337-42 (1998).
Cohen, et al, 'Risk for new onset of depression during the menopausal transition: the Harvard study of moods and cycles' Arch. Gen. Psychiatry. 63(4):385-90 (2006).
Dasilva and Van Lier, 'Synthesis and structure-affinity of a series of 7 alpha-undecylestradiol derivatives: a potential vector for therapy and imaging of estrogen-receptor-positive cancers', J. Med, Chem., 33(1):430-4 (1990).
Espeland, et al, 'Conjugated equine estrogens and global cognitive function in postmenopausal women: Women's Health Initiative Memory Study', JAMA, 291 (24):2959-68 (2004).
Freeman, et al, 'Associations of hormones and menopausal status with depressed mood in women with no history of depression', Arch. Gen. Psychiatry, 63(4):375-82 (2006).
Freeman, et al, 'Hormones and menopausal status as predictors of depression in women in transition to menopause' Arch. Gen. Psychiatry, 61(462-70 (2004).
Gao, et al., 'The relationships between age, sex, and the incidence of dementia and Alzheimer disease: a meta analysis', Arch. Gen. Psychiatry, 55(9):809-15 (1998).
Gustafsson, et al, 'What pharmacologists can learn from recent advances in estrogen signalling', Trends Pharmacol Sci., 24(9):479-85 (2003).
Hadley, et al., The future of aging therapies'. Cell, 120(4):557-67 (2005).
Henderson, et al, 'Postmenopausal hormone therapy and Alzheimer's disease risk: interaction with age', J. Neural. Neurosurg. Psychiatry, 76(1):103-5 (2005).

(Continued)

Primary Examiner — Jeffrey S. Lundgren
Assistant Examiner — Sara E Townsley
(74) Attorney, Agent, or Firm — Pabst Patent Group LLP

(57) ABSTRACT

Select phytoestrogen pharmaceutical compositions and methods of use for promoting neurological heath and prevention of age-related neurodegeneration, such as AD, have been developed. These select phytoestrogen formulations are composed of a number of plant-derived estrogenic molecules and/or their structural analogues and exhibit binding preference to ERβ over ERα and agonist activity in the brain. These ERβ-selective phytoestrogen formulations cross the blood-brain-barrier and promote estrogen-associated neurotrophism and neuroprotections mechanisms in the brain, without activating proliferative mechanisms in the reproductive tissues and are therefore devoid of other estrogen-associated problematic aspects. These are administered enterally, transdermally, transmucosally, intranasally or parenterally, in a dosage effective to prevent or alleviate neuronal damage, effect neuronal regeneration or sustain viability, increase expression of anti-apoptotic proteins, and/or decrease indicators of Alzheimer's Disease.

6 Claims, 17 Drawing Sheets

(56) References Cited

OTHER PUBLICATIONS

Hogervorst, et al, 'Hormone replacement therapy for cognitive function in postmenopausal women', Cochrane Database Syst. Rev., 3):CD003122. (2002).

http://www.ninds.nih.gov/disorders/disorder_index.htm, National Institute of Neurological Disorders and Stroke website.

Kreijkamp-Kaspers, et al, 'Effect of soy protein containing isoflavones on cognitive function, bone mineral density, and plasma lipids in postmenopausal women: a randomized controlled trial', JAMA, 292(1):65-74 (2004).

Kuiper, et al., "Interaction of estrogenic chemicals and phytoestrogens with estrogen receptor$^2$", Endocrinology, 139(10):4252-63 (1998).

Manson, et al, 'Postmenopausal hormone therapy: new questions and the case for new clinical trials', Menopause, 13(1):139-47 (2006).

Meyers, et al, 'Estrogen receptor-beta potency-selective ligands: structure-activity relationship studies of diarylpropionitriles and their acetylene and polar analogues', J. Med. Chem., 44(24):4230-51 (2001).

Morito, et al., "Interaction of phytoestrogens with estrogen receptors a and $^2$", Biol. Pharm. Bull., 24(4):351-56 (2001).

Morrison, et al, 'Lack of efficacy of estradiol for depression in postmenopausal women: a randomized, controlled trial' Biol. Psychiatry, 15;55(4):406-12 (2004).

Mueller, et al. Phytoestrogens and Their Human Metabolites Show Distinct Agonistic and Antagonistic Properties on Estrogen Receptor a (ERa) and ERb in Human Cells. Tox. Sci. 80, pp. 14-25, 2004.

North American Menopause Society. (2004) The menopause practice: a clinician's guide htto://www.menopause.oro/aboutmeno/overview.htm.

Olshansky, et al., 'Position statement on human aging', J. Gerontol. A Biol. Sci. Med. Sci., 57(8):B292-7 (2002).

Olshansky, et al., "No truth to the fountain of youth", Scientific American, 92-95 (2002).

Resnick, et al, 'Hormone therapy and risk of Alzheimer disease: a critical time', JAMA, 288(17):2170-2 (2002).

Schmidt, et al, 'A longitudinal evaluation of the relationship between reproductive status and mood in perimenopausal women', Am. J. Psychiatry, 161 (12):2238-44 (2004).

Schmidt, et al, 'Estrogen replacement in perimenopause-related depression: a preliminary report', Am J Obstet Gynecol., 183(2):414-20 (2000).

Schmidt, et al, 'Mood, depression, and reproductive hormones in the menopausal transition', Am. J. Med., 118 Suppl 12B:54-8 (2005).

Shumaker, et al, "Conjugated equine estrogens and incidence of probable dementia and mild cognitive impairment in postmenopausal women: Women's Health Initiative Memory Study." JAMA, 291(24):2947-58 (2004).

Soares, et al, "Efficacy of estradiol for the treatment of depressive disorders in perimenopausal women: a double-blind, randomized, placebo-controlled trial" Arch. Gen. Psychiatry, 58(6):529-34 (2001).

Stauffer, et al, 'Pyrazole ligands: structure-affinity/activity relationships and estrogen receptor-alpha-selective agonists' J. Med. Chem., 43(26):4934-4947 (2000).

Sun, et al, 'Molecular basis for the subtype discrimination of the estrogen receptor-beta-selective ligand, diarylpropionitrile' MoMot. EndocrinoL, 17(2):247-58 (2003).

Usui, et al., 'Pharmaceutic& prospects of phytoestrogens', Endocrine Journal, 53110-20 (2006).

Vijg and Campisi, 'Puzzles, promises and a cure for ageing'. Nature, 454 (7208):1065-71 (2008).

Wakeling, et al., "A potent specific pure antiestrogen with clinical potential", Cancer Res, 51:3867 (1991).

Wassertheil-Smoller, et al, Depression and cardiovascular sequelae in postmenopausal women. The Women's Health Initiative (WHI) Arch. Intern. Med., 164(3):289-98 (2004).

Weihua, et al, 'Update on estrogen signaling', FEES Lett., 546(1):17-24 (2003).

Yaffe, et al, "Estrogen therapy in postmenopausal women: effects on cognitive function and dementia" JAMA, 279(9):688-95 (1998).

Zandi, et al, 'Hormone replacement therapy and incidence of Alzheimer disease in older women: the Cache County Study', JAMA, 288(17):2123-2129(2002).

Zhao, et al, "Neuroprotective and neurotrophic efficacy of phytoestrogens in cultured hippocampal neurons", Exp. Biol. Med. (Maywood), 27(7):509-19 (2002).

Zhao, et al., 'Design, synthesis, and estrogenic activity of a novel estrogen receptor modulator-a hybrid structure of 17beta—estradiol and vitamin E in hippocampal neurons', J. Med. Chem., 50(18):4471-4481 (2007).

Zhao, et al., 'Estrogenic agonist activity of IC1182,780 (Feslodex) in hippocampal neurons: implications for basic science understanding of estrogen signaling and development of estrogen modulators with a dual therapeutic profile', J. Pharmacol. Exp. Ther., 319(3):1124-32 (2006).

Zhao, et al. '2004 Abstract Book; The Keystone Symposia: Nuclear Receptors: Steroid Sisters', Keystone, CO; Feb. 2004.

Zweifel, et al, 'A meta-analysis of the effect of hormone replacement therapy upon depressed mood' Psychoneuroendocrinology, 22(3):189-212 (1997).

Kinjo,"Phytoestrogens",Nippon, Rinsho, 58(12):60-64 (2000).

Hedlund, et al., "Prostatic fluid concentrations of isoflavonoids in soy consumers are sufficient to inhibit growth of benign and malignant prostatic epithelial cells in vitro", Prostate, 66(5):557-66 (2006).

\* cited by examiner

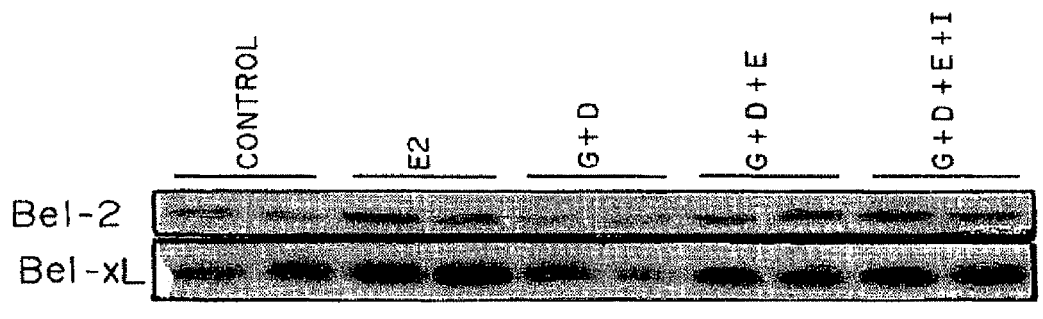
FIG. 4A
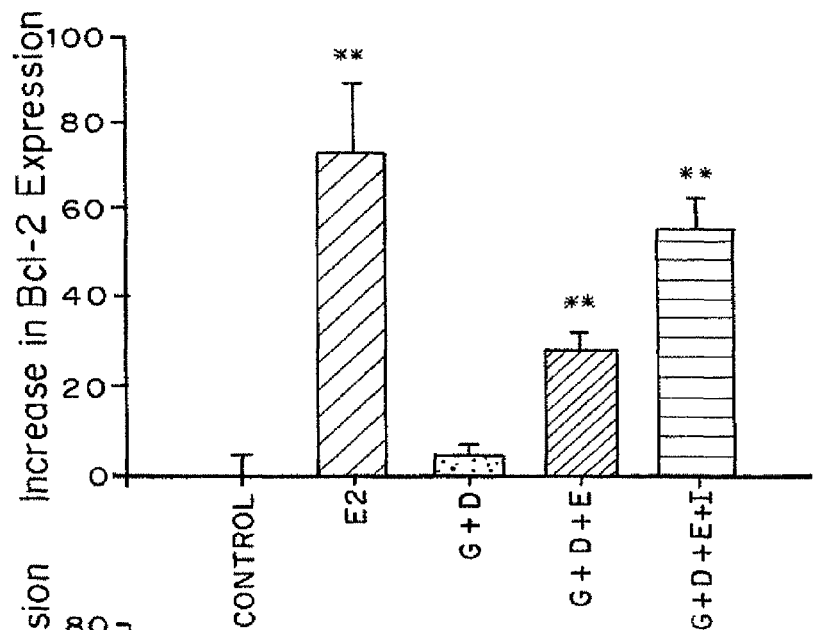
FIG. 4B
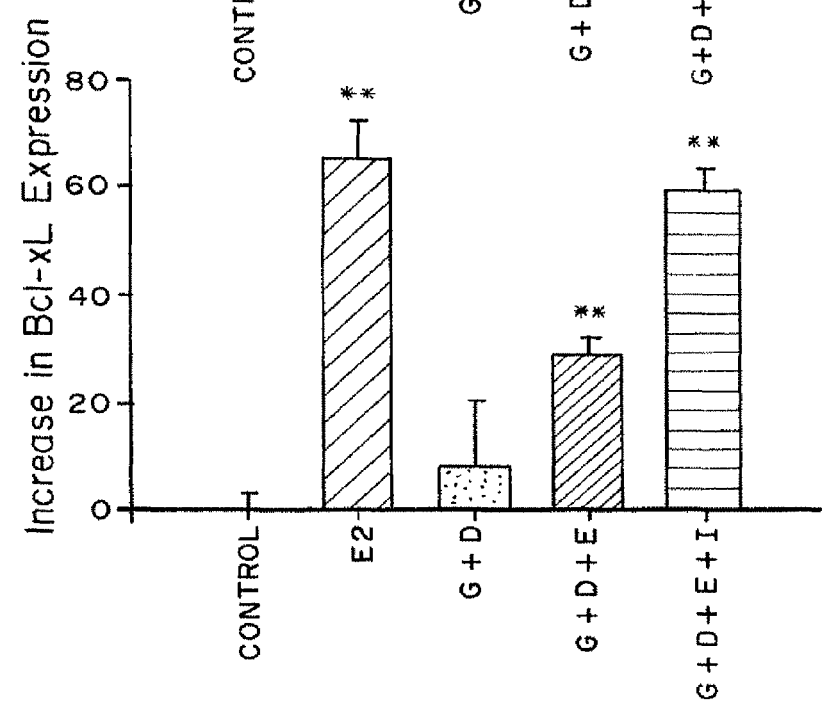

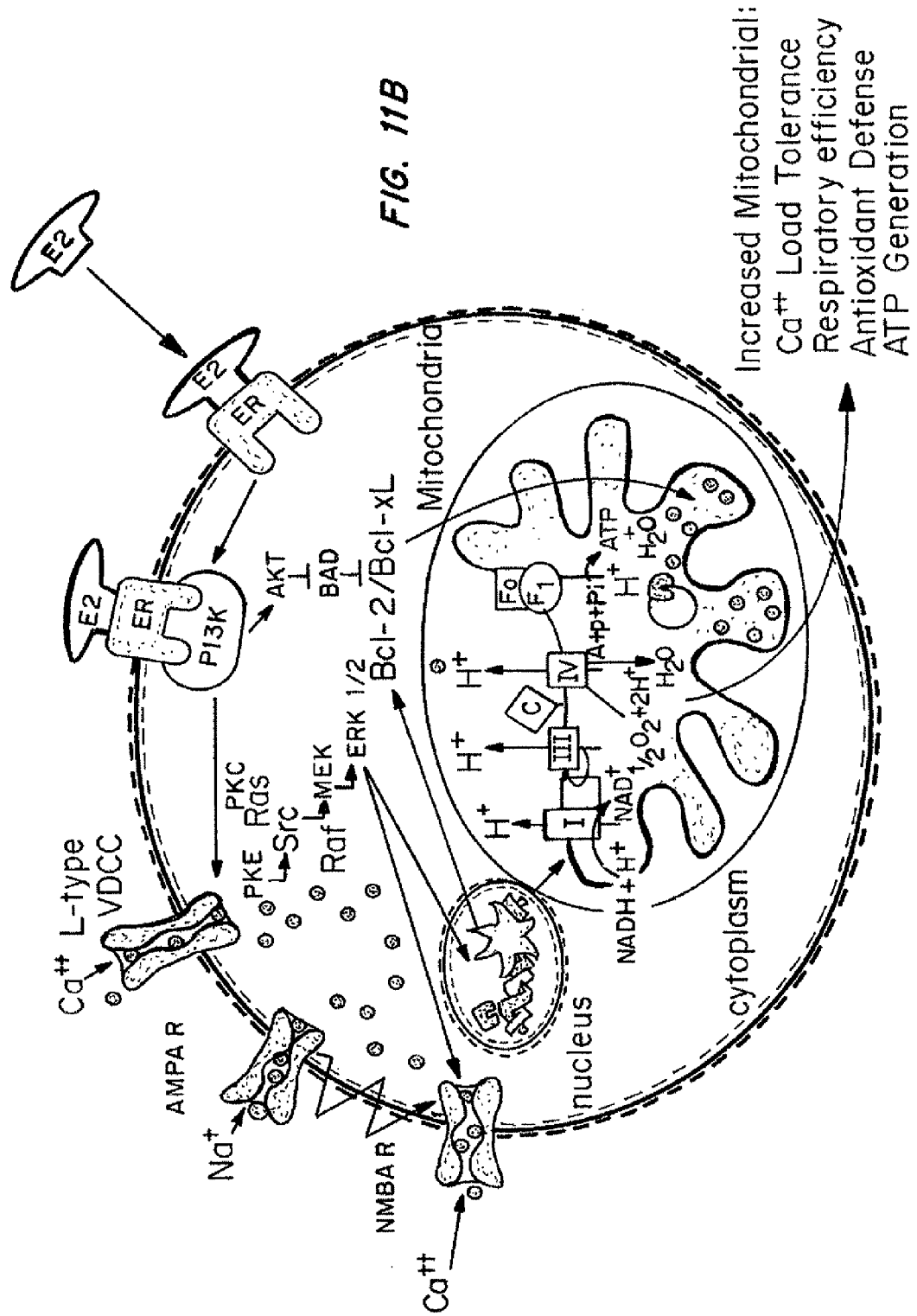

PHYTOESTROGENIC FORMULATIONS FOR ALLEVIATION OR PREVENTION OF NEURODEGENERATIVE DISEASES

CROSS-REFERENCE TO RELATED APPLICATIONS

This application is a divisional of prior application U.S. Ser. No. 11/777,951 filed Jul. 13, 2007, entitled Phytoestrogenie Formulations for Alleviation or Prevention of Neurodegenerative Diseases", by Roberta Diaz Brinton and Liqin Zhao, which claims priority to U.S. Ser. No. 60/819,849 accorded a filing date of Aug. 2, 2006, U.S. Ser. No. 60/889,920 filed Feb. 14, 2007, and U.S. Ser. No. 60/943,190 filed Jun. 11, 2007, all of which are herein incorporated in their entirety by reference.

BACKGROUND OF THE INVENTION

The demographics suggest that we face a devastating increase in the prevalence of AD, reinforcing the immediate need for basic and translational neuroscience to develop safe and efficacious ET and HT regimens for the brain. Of those affected with AD, 68% are female and 32% are male (Brookmeyer et al., 1998 Am J Public Health 88:13372). Because women have a longer life expectancy than men, the absolute number of women with AD exceeds that of men. However, a double danger exists for women. Results of a meta-analysis of seven sex-specific studies concluded that women are 1.5 times more likely to develop AD than age-matched men (Gao et al., 1998 Arch Gen Psychiatry 55:809), which was supported by the Cache County analysis that showed a clear female gender increase in the incidence of AD (Zandi et al., 2002 JAMA 288:21239).

At the turn of the new millennium in the United States, there were nearly 42 million women over the age of 50 years and, of these, more than 31 million women were over the age of 55 years (North American Menopause Society, 2004). Worldwide, there are currently more than 470 million women aged 50 years or older, and 30% of those are projected to live into their 80s (North American Menopause Society, 2004). These women can anticipate spending one-third to one-half of their lifetime in the menopausal state. Reports on prevalence of AD vary, but of the 18 million American women in their mid to late 70s, as many as 5 million may suffer from AD, and this figure increases dramatically at older ages (Brookmeyer et al., 1998). The projected exponential increase in the prevalence of AD, along with the anticipated impact on families and society, highlights the imperative for developing strategies to prevent or delay the onset of AD sooner rather than later.

The profound disparities between the largely positive basic science findings of gonadal steroidal action in brain and the adverse outcomes of recent estrogen or hormone therapy ("ET/HT") clinical trials in women who are either aged postmenopausal or postmenopausal with Alzheimer's disease (AD), has led to an intense reassessment of gonadal hormone action and the model systems used in basic and clinical science. One key factor that could contribute to the negative results of the Women's Health Initiative Memory Study ("WHIMS") trial was the advanced age, more than ten years following menopause, at which ET/HT was initiated in women. Data from both basic science analyses and clinical studies indicate a "healthy cell bias" of estrogen action in the neurons/brains, suggesting that ET/HT acts as an effective preventative therapeutic strategy for age-related cognitive decline and neurodegenerative disorders, such as Alzheimer's disease ("AD"), while it is not an effective treatment strategy.

The current widely prescribed ET, conjugated equine estrogens ("CEE"), is a highly complex ET with over 200 different components. Whether CEE provides the optimal therapeutic efficacy has been questioned. Another key issue challenging HT is the optimal composition. The progestin and its timing of administration in conjunction with ET, remains to be determined. Moreover, while ET/HT has long been used in postmenopausal women to delay or reverse some of the problems associated with menopause, epidemiological and clinical studies have uncovered potential long-term risks related to this therapy. The recently revealed risks associated with ET/HT have greatly increased interest in the development of estrogen alternatives that promote beneficial effects of estrogen in brain, bone and the cardiovascular system, while not eliciting deleterious effects in other organs, particularly in breast and uterine tissues.

Two nuclear receptors for estrogen (ERs), ERα and ERβ, have been identified. In the central nervous system, both ERα and ERβ are expressed in the hippocampus and cortex of rodent and human brains. Previous studies have demonstrated that both ERα and ERβ can equivalently promote neuronal survival by activating estrogen mechanisms of action in rat hippocampal neurons. Increasing evidence indicates that ERβ is a key requirement for activation of mechanisms that underlie estrogen-inducible neuronal morphological plasticity, brain development, and cognition. ERα, on the other hand, is more predominant in mediating the sexual characteristics of estrogen effects in the reproductive organs such as breast and uterus. Taken together, these data establish a potential therapeutic application for ERβ as a pharmacological target to promote memory function and neuronal defense mechanisms against age-related neurodegeneration such as Alzheimer's disease (AD), while avoiding activating untoward estrogenic proliferative effects in the breast and uterus, although this might be at the cost of lower efficacy due to the lack of activation of ERβ in the brain. Other potential therapeutic advantages associated with ERβ include regulation of estrogen vasculoprotective action and development of interventions targeting diseases such as depression, colon cancer, prostate cancer, obesity, leukemia, and infertility. However, a potential disadvantage of an ERβ-selective ligand is the lack of activation of ERα in bone, as ERα has been demonstrated to mediate estrogen regulation of bone density.

Although there is still controversy regarding the differential roles of two estrogen receptor ("ER") subtypes, ERα and/or ERβ, in mediating estrogen actions in the brain and/or neurons, it has been widely demonstrated that ERβ plays a key role in regulating brain development, neurogenesis and estrogen-induced improved neuronal plasticity and survival. In addition, as compared with ERα, ERβ is less effective in mediating the sexual characteristics of estrogen action in reproductive tissues, avoiding activating untoward estrogenic proliferative effects in the breast and uterus. Therefore, ERβ represents a potentially safer therapeutic target for promoting memory function and neuroprotection. However, this safety may be at the cost of lower efficacy, due to the lack of activation of Ma in the brain. Other potential advantages for ERβ-target therapeutics arise from its regulation of estrogen's cardioprotective effects. ERβ-selective ligands may also provide effective therapeutics for preventing or treating inflammation, depression, anxiety, colon cancer, prostate cancer, obesity, leukaemia, and infertility.

In searching for an effective ERβ-selective estrogen alternative replacement therapy for promoting neurological function and preventing age-related neurodegeneration, such as AD, in postmenopausal women, it is of particular interest to identify and develop naturally occurring molecules or analogues that potentially have a less toxic profile for long-term administration. It is known that several plant-derived estrogenic molecules (referred to as "phytoestrogens") bind to ERα and to ERβ subtypes, and some of these molecules possess moderate binding selectivity for ERβ and exert estrogenic effects in multiple tissues.

The therapeutic efficacy of phytoestrogens in the brain remains controversial. On the one hand, when administered singly, phytoestrogens appeared to be moderately neuroprotective. On the other hand, a recent clinical trial revealed that a soy protein supplement that contains a mixture of phytoestrogens did not show improved cognitive function in postmenopausal women, when treatment was initiated at the age of 60 years or older. The clinical trial of phytoestrogens reported that a soy protein supplement containing a complex formulation of isoflavones did not improve cognitive function in postmenopausal women when treated at the age of 60 years or older, Kreijkamp-Kaspers, et al. *JAMA* 2004, 292, 65-74, also indicating that when started 10 or more years following menopause in postmenopausal women when age-related neuronal reorganization has taken place, ET/HT has no benefit on neural function. Age and hormonal "history" may be important factors that were responsible for these negative results, as was the case for the WHIMS trials.

Another issue that can substantially impact the efficacy of a mixture of phytoestrogens action in the brain is the formulation of phytoestrogens, since when administered alone, a number of phytoestrogens were protective to neurons from neurodegenerative insults. Zhao, et al. *Exp. Biol. Med.* 2002, 227, 509-519. Soy extracts or soy protein supplements generally contain multiple phytoestrogenic molecules, some of which may be ERα-selective agonists, while others may be ERβ-selective agonists, and others may be ineffective in activating either ERα or ERβ but may function as inhibitors of ER binding of those ERα and/or ERβ phytoestrogenic agonists. The ineffectiveness of a complex formulation of phytoestrogens in promoting beneficial effects of estrogen in brain, such as a soy-derived preparation, may also arise from antagonizing actions among the different phytoestrogens, in addition to the possible ER antagonism, likely from the activation of both ERα and ERR in the same context. Co-administration of an ERα-selective agonist and an ERβ-selective agonist is less effective than treatment with either agonist alone in various neuroprotective measurements.

ERα and ERβ have a yin/yang relationship in many contexts where one receptor may antagonize the actions of the other. Weihua, et al. *FEES Lett.* 2003, 546, 17-24; Gustafsson, J. A. *Trends Pharmacol. Sci.* 2003, 24, 479-485. Studies confirmed this observation, showing that coadministration of ERα-selective agonist PPT and ERβ-selective agonist DPN was less efficacious than either PPT or DPN alone in protecting hippocampal neurons against excitotoxic insults. Based on this analysis, a presumption can be made that the ineffectiveness of administering a mixture of phytoestrogens (i.e. a soy protein supplement) may partly come from the antagonizing actions among different phytoestrogens, which may be ERα selective or ERβ selective. These findings indicate that although both ERα and ERβ contribute to estrogen promotion of neuronal survival, simultaneous activation of both ER subtypes, ERα and ERβ, in the same context may diminish the efficacy. In addition, the different ratio and distinct function of homodimer and heterodimer induced by co-administration of an ERα-selective agonist and an ERβ-selective agonist may also account for the reduced efficacy exerted by the combination of both agonists.

Development of an ERβ-selective phytoestrogen formulation could maximize the therapeutic benefits associated with activation of ERβ in the brain while minimizing the adverse effects associated with the activation of ERα in reproductive tissues. Moreover, selective targeting of ERβ potentially reduces antagonistic actions that may occur in a complex soy-derived preparation. This naturally occurring ideal formulation would have tremendous therapeutic value in promoting neurological function and preventing AD in a population at risk for losing neurological capacity and losing memory function, i.e., postmenopausal women. To date, no such phytoestrogen formulation exists. Thus, there is a need to discover and develop a novel select phytoestrogen formulation, generally, and particularly, a formulation that functions in the brain.

It is therefore an object of the present invention to provide an ERβ-selective phytoestrogen formulation maximizing the therapeutic benefits associated with activation of ERβ in the brain while minimizing the adverse effects associated with the activation of ERα in reproductive tissues.

It is a further object of the invention to provide such a composition wherein the active ingredients are isolated from natural substances.

SUMMARY OF THE INVENTION

Select phytoestrogen pharmaceutical compositions and methods of use for promoting neurological health and prevention of age-related neurodegeneration, such as AD, have been developed. These select phytoestrogen formulations are composed of a number of plant-derived estrogenic molecules and/or their structural analogues and exhibit binding preference to ERβ over ERα and agonist activity in the brain. These ERβ-selective phytoestrogen formulations cross the blood-brain-barrier and promote estrogen-associated neurotrophism and neuroprotection mechanisms in the brain, without activating proliferative mechanisms in the reproductive tissues and are therefore devoid of other estrogen-associated problematic aspects. The select phytoestrogen formulations are therapeutically useful to both women and men for sustaining neurological health and preventing age-related cognitive decline and neurodegenerative disorders, such as AD.

These are administered enterally, transdermally, transmucosally, intranasally or parenterally, in a dosage effective to prevent or alleviate neuronal damage, effect neuronal regeneration or sustain viability, increase expression of anti-apoptotic proteins, and/or decrease indicators of Alzheimer's Disease. The formulations preferably contain combinations of compounds, and can be formulated for daily, sustained, delayed or weekly/monthly administration. In a preferred embodiment, these are administered to women who are in menopause or post menopausal, most preferably early in menopausal.

BRIEF DESCRIPTION OF THE DRAWINGS

FIGS. 4A and 4B are graphs showing the effect of four ERβ-selective phytoestrogenic molecules when co-administered (100 nM) for all four molecules) as G+D, G+D+E, or G+D+E+I, on the expression of the anti-apoptotic proteins, Bcl-2 and Bcl-xL, in primary hippocampal neurons.

FIGS. 11A-11C are schematics showing estrogen mechanisms of action that lead to neurotrophic and neuroprotective outcomes. 11A, 17-β-Estradiol (E2) acting via a membrane-associated site (mER) activates a cascade required for multiple responses that lead to enhanced neural plasticity, morphogenesis, neurogenesis, and neural survival. The signaling sequence induced by E2 at the membrane site is as follows: (1) E2 binding to mER, (2) E2-mER complexes with p85 to activate PI3K, (3) activating calcium-independent PKC, (4) phosphorylating the L-type calcium channel, (5) inducing calcium influx, (6) activating calcium-dependent PKCs, (7) activating Src kinase, (8) activating the MEK/ERK1/2 pathway, (9) ERK translocates to the nucleus, (10) activating and phosphorylating CREB, (11) enhancing transcription of anti-apoptotic genes Bcl-2 and Bcl-xl, which enhance mitochondrial vitality, and spinophilin, which encourages synaptic growth, (12) simultaneously, estrogen activation of PI3K leads to activation of Akt, which phosphorylates and inhibits the proapoptotic protein BAD. 11B, Estrogen-induced neuroprotective mechanisms converge on mitochondria. Estrogen-activated cellular signaling cascade promotes enhanced mitochondrial function, leading to increased calcium load tolerance, enhanced electron transport chain efficiency, and promotion of antioxidant defense mechanisms. These actions are mediated by the regulation of both nuclear and mitochondrial encoded genes initiated by the activation of second-messenger signaling cascades. 11C, Conceptual schematic of NeuroSERM design and therapeutic use. Consistent with the healthy cell bias of estrogen benefit hypothesis, selective molecules would be administered before neurodegenerative insult while neurons are still healthy. NeuroSERM exposure would lead to enhanced neural survival mechanisms, represented as mitochondria with Bcl-2 additions, that promote neural defense against neurodegenerative insults associated with age-associated diseases such as Alzheimer's and Parkinson's. Designer NeuroSERM molecules target the membrane site of estrogen action, whereas PhytoSERM molecules preferentially target estrogen receptorβ. Abbreviations: AMPAR, AMPA receptor; C, cytochrome oxidase; $F_0$, $F_1$, ATPase subunits; LTD, long-term depression; LTP, long-term potentiation; NAD, nicotinamide adenine dinucleotide; NADH, nicotinamide adenine dinucleotide; VDCC, voltage-dependent calcium channel.

DETAILED DESCRIPTION OF THE INVENTION

I. Definitions

Figure 1:
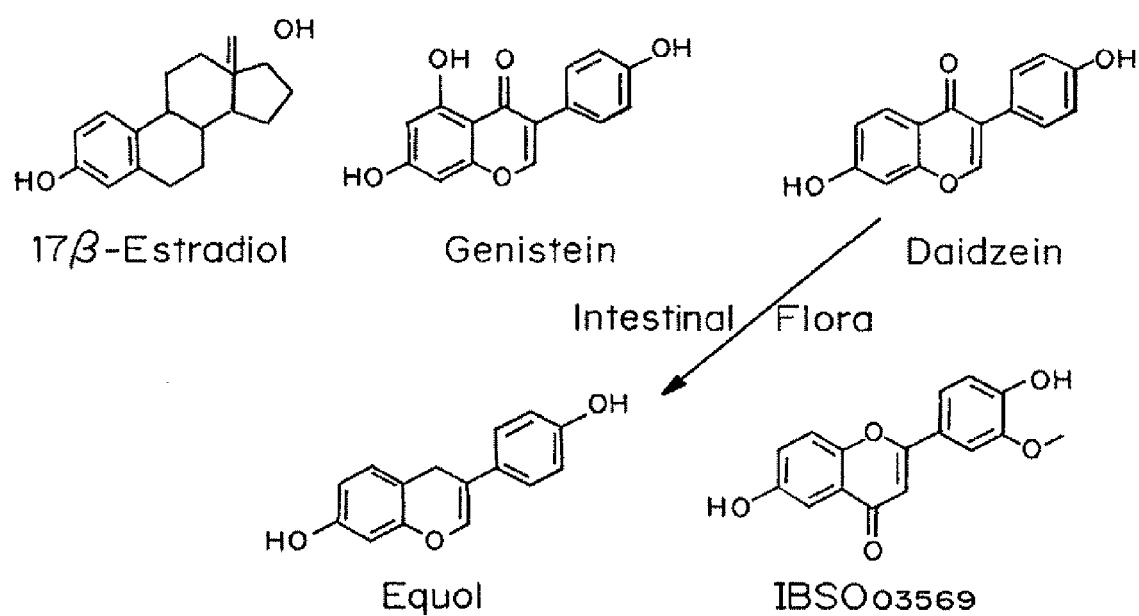
FIG. 1 shows the chemical Structures of 17β-estradiol and the phytoSERMs genistein, daidzein, equol, and IBSO03569.

"Estrogen Receptor", as used herein, refers to any protein in the nuclear receptor gene family that binds estrogen, including, but not limited to, any isoforms and variants thereof. Human estrogen receptors include the alpha- and beta-isoforms (referred to herein as "ERα" and "ERβ").

"Estrogen Receptor Modulator", as used herein, refers to a compound that can act as an estrogen receptor agonist or antagonist of an estrogen receptor or estrogen receptor isoform having an $IC_{50}$ or $EC_{50}$ with respect to ERα, ERβ and/or other estrogen receptor isoforms of no more than about 50 μM as determined using the ERα, and/or ERβ transactivation assay described herein. More typically, estrogen receptor modulators have $IC_{50}$ or $EC_{50}$ values (as agonists or antagonists) of not more than about 10 μM. Representative compounds are predicted to exhibit agonist or antagonist activity via an estrogen receptor. Compounds preferably exhibit an antagonist or agonist $IC_{50}$ or $EC_{50}$ with respect to ERα and/or ERβ of about 10 μM, more preferably, about 500 nM, even more preferably about 1 nM, and most preferably, about 500 pM, as measured in the ERα and/or ERβ transactivation assays. "$IC_{50}$" is that concentration of compound which reduces or inhibits the activity of a target (e.g., ERα or ERβ) to half-maximal level. "$EC_{50}$" is that concentration of compound which provides half-maximum effect.

"Selective Estrogen Receptor Modulator" (or "SERM"), as used herein, refers to a compound that exhibits activity as an agonist or antagonist of an estrogen receptor (e.g., ERα, ERβ or other estrogen receptor isoform) in a tissue-dependent or receptor dependent manner. Thus, as will be apparent to those of skill in the biochemistry, molecular biology and endocrinology arts, compounds that function as SERMs can act as estrogen receptor agonists in some tissues, e.g., bone, brain, and/or cardiovascular, and as antagonists in other tissue types, e.g., the breast and/or uterine tissue.

"Phytoestrogen" refers to a naturally occurring compound of plants, such as soybeans, or plant products, such as whole grain cereals, that acts like estrogen or binds to an estrogen receptor.

As used herein, the term "NeuroSERM" refers to compounds that target the membrane site of estrogen action.

As used herein, the term "PhytoSERM" refers to natural source compounds that preferentially target estrogen receptor beta.

As used herein, the term "analogue" refers to a chemical compound with a structure similar to that of another (reference compound) but differing from it in respect to a particular component, functional group, atom, etc.

As used herein, the term "derivative" refers to compounds which are formed from a parent compound by chemical reaction(s).

II. Compositions

Compositions containing one or more phytoestrogens are described herein. A number of phytoestrogens have been isolated and identified and additional analogs created, all of which have estrogen receptor binding selectivity. In one embodiment, of the composition contains two or more plant-derived estrogenic molecules and/or structural analogues, which possess ERβ-binding selectivity and exhibit neuroprotective activity when administered individually. These compositions are useful for preventing estrogen-deficiency associated symptoms and disorders, particularly age-related cognitive decline and neurodegenerative diseases, such as Alzheimer's disease ("AD").

A. PhytoSERMs

The compositions described herein contain one or more phytoestrogens or natural source selective estrogen receptor modulators (SERMs) exhibiting a binding preference for ERβ. PhytoSERMs can be identified as described in Example 1. Suitable phytoSERMs include, but are not limited to, genistein, daidzein, equol, IBSO03569 and combinations thereof. The structures of genistein, daidzein, equol, and IBSO03569 are shown in FIG. 1. Others are listed in Table 1. Preferred compounds cross the blood brain barrier.

As demonstrated by Example 2, combinations of two or more PhytoSERMS are more effective than administration of one PhytoSERM.

The compounds can be used in the form of salts derived from inorganic or organic acids. These salts include, but are not limited to, the following: acetate, adipate, alginate, citrate, aspart ate, benzoate, benzenesulfonate, bisulfate, butyrate, camphorate, camphorsulfonate, digluconate, cyclopentanepro-pionate, dodecylsulfate, ethanesulfonate, glucoheptanoate, glycerophosphate, hemi-sulfate, heptanoate, hexamate, fumarate, hydrochloride, hydrobromide, hydroiodide, 2-hydroxyethanesulfonate, lactate, maleate, methanesulfonate, nicotinate, 2-napthalenesulfanate, oxalate, pamoate, pectinate, sulfate, 3-phenylpropionate, picrate, pivalate, propionate, succinate, tartrate, thiocyanate, p-toluenesulfonate and undecanoate. Also, any basic nitrogen-containing groups can be quaternized with agents such as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Wafer or oil-soluble or dispersible products are thereby obtained.

Examples of acids which may be employed to form pharmaceutically acceptable acid addition salts include such inorganic acids as hydrochloric acid, sulfuric acid, and phosphoric acid, and organic acids such as oxalic acid, maleic acid, succinic acid and citric acid. Basic addition salts can be prepared in situ during the final isolation and purification of the compounds, or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, and aluminum salts, as well as non-toxic ammonium, quaternary ammonium, and mine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, and piperazine.

Appropriate carriers can be added that assist the compounds to cross the blood-brain-barrier.

B. Additional Active Agents

While the compounds can be administered as the sole active pharmaceutical agent, they can also be used in combination with one or more other compound as described herein, and/or in combination with other agents used in the treatment and/or prevention of estrogen receptor-mediated disorders. Alternatively, the compounds can be administered sequentially with one or more such agents to provide sustained therapeutic and prophylactic effects. Suitable agents include, but are not limited to, other SERMs as well as traditional estrogen agonists and antagonists.

Representative agents useful in combination with the compounds for the treatment of estrogen receptor-mediated disorders include, for example, tamoxifen, 4-hydroxytarnoxifen, raloxifene, toremifene, droloxifene, TAT-59, idoxifene, RU 58,688, EM 139, ICI 164,384, ICI 182,780, clomiphene, MER-25, DES, nafoxidene, CP-336,156, GW5638, LY 139481, LY353581, zuclomiphene, enclomiphene, ethamoxytriphetol, delmadinone acetate, bisphosphonate. Other agents that can be combined with one or more of the compounds include aromatase inhibitors such as, but not limited to, 4-hydroxymdrostenedione, plomestane, exemestane, aminogluethimide, rogletimide, fadrozole, vorozole, letrozole, and anastrozole.

Still other agents useful in combination with the compounds described herein include, but are not limited to antineoplastic agents, such as alkylating agents, antibiotics, hormonal antineoplastics and antimetablites. An example includes the compounds used to treat or prevent osteoporosis. Other ingredients include vitamins, nutritional supplements, anti-oxidant agents, coenzymes, etc.

The additional active agents may generally be employed in therapeutic amounts as indicated in the PHYSICIANS' DESK REFERENCE (PDR) 53rd Edition (2003), or such therapeutically useful amounts as would be known to one of ordinary skill in the art. The compounds and the other therapeutically active agents can be administered at the recommended maximum clinical dosage or at lower doses. Dosage levels of the active compounds in the compositions may be varied to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

C. Pharmaceutical Compositions

The compounds can be administered enterally, transdermally, transmucisally, intranasally or parenterally. Excipients for oral formulation are known to those skilled in the art, as discussed briefly below, and can be used to provide immediate, sustained, delayed, or pulsed release. The compounds can also be administered via a transdermal patch, a depo, vaginally or rectally using a topical carrier such as a gel, lotion, ointment, liposomal formulation, suspension, foam, spray or suppository, via the pulmonary or nasal route, buccally or sublingual via the mucosal membranes of the mouth. The appropriate excipients for all of these formulations are known. The compounds may be dissolved or suspended in saline, sterile water or phosphate buffered saline, or a suitable oil for injection iv, im, subcu, or ip.

Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-.beta.-cyclodextrin, polyvinylpyrrollidone, low melting waxes, and ion exchange resins, as well as combinations of any two or more thereof. Other suitable pharmaceutically acceptable excipients are described in Remington's Pharmaceutical Sciences, Mack Pub. Co., New Jersey (1991).

Pharmaceutical compositions containing estrogen receptor modulating compounds may be in any form suitable for the intended method of administration, including, for example, a solution, a suspension, or an emulsion. Liquid carriers are typically used in preparing solutions, suspensions, and emulsions. Liquid carriers contemplated for use include, for example, water, saline, pharmaceutically acceptable organic solvent(s), pharmaceutically acceptable oils or fats, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, or stabilizers. Suitable organic solvents include, for example, monohydric alcohols, such as ethanol, and polyhydric alcohols, such as glycols. Suitable oils include, for example, soybean oil, coconut oil, olive oil, safflower oil, cottonseed oil. For parenteral administration, the carrier can also be an oily ester such as ethyl oleate, isopropyl myristate. Compositions may also be in the form of microparticles, microcapsules, liposomal encapsulates, as well as combinations of any two or more thereof.

The compounds may be administered orally, parenterally, sublingually, by inhalation spray, rectally, vaginally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water; Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid can be useful in the preparation of injectables.

Suppositories for rectal or vaginal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifing and suspending agents, cyclodextrins, and sweetening, flavoring, and perfuming agents.

The compounds can also be administered in the form of lipsomes. As is known in the art, liposomes are generally derived from phospholipids or other lipid substances. Liposomes are formed by mono- or multilamellar hydrated liquid crystals that are dispersed in an aqueous medium. Any nontoxic, physiologically acceptable and metabolizable lipid capable of forming liposomes can be used. The present compositions in liposome form can contain, in addition to a compound, stabilizers, preservatives, excipients. The preferred lipids are the phospholipids and phosphatidyl cholines (lecithins), both natural and synthetic. Methods to form liposomes are known in the art (Prescott 1976).

Transdermal patches are well known for delivery of nicotine, nitroglycerin and birth control. These can be utilized with these formulations as well. Depos that are implanted under the skin or ip can also be used, similarly to the manner of delivering birth control.

III. Methods of Administration

Compounds can be administered in a variety of ways including enteral, parenteral, pulmonary, nasal, mucosal and other topical or local routes of administration. For example, suitable modes of administration include oral, subcutaneous, transdermal, transmucosal, iontophoretic, intravenous, intramuscular, intraperitoneal, intranasal, subdural, rectal, vaginal and inhalation.

An effective amount of the compound or composition is administered to treat and/or prevent an estrogen receptor-mediated disorder in a human or animal subject. Modulation of estrogen receptor activity results in a detectable suppression or up-regulation of estrogen receptor activity either as compared to a control or as compared to expected estrogen receptor activity. Effective amounts of the compounds generally include any amount sufficient to detectably modulate estrogen receptor activity by any of the assays described herein, by other activity assays known to those having ordinary skill in the art, or by detecting prevention and/or alleviation of symptoms in a subject afflicted with an estrogen receptor-mediated disorder.

The effective amount will also be determined based on when the compounds are administered. Estrogen/hormone therapy (ET/HT) has been associated with the reduced risk of developing AD when treated at the menopausal transition in women Brinton, R. D. Impact of estrogen therapy on Alzheimer's disease: a fork in the road? *CNS Drugs* 2004, 18, 405-422. For example, results of the Cache County Study indicate that women who receive ET/HT at the time of menopause and continue for 10 years have a 3-fold lower risk of developing AD, Zandi, et al. *JAMA* 2002, 288, 2123-2129, whereas the recent data from the Women's Health Initiative Memory Study indicate that women who begin the therapy late in menopause have a greater risk of developing AD, Espeland, et al. Women's Health Initiative Memory Study. *JAMA* 2004, 291, 2959-2968; Shumaker, et al., *JAMA* 2004, 291, 2947-2958. These clinical observations are consistent with basic science analyses of estrogen-inducible molecular mechanisms in the brain, indicating a healthy cell bias of estrogen action.

Estrogen receptor-mediated disorders that may be treated include any biological or medical disorder in which estrogen receptor activity is implicated or in which the inhibition of estrogen receptor potentiates or retards signaling through a pathway that is characteristically defective in the disease to be treated. The condition or disorder may either be caused or characterized by abnormal estrogen receptor activity. Representative estrogen receptor-mediated disorders include, for example, osteoporosis, atherosclerosis, estrogen-mediated cancers (e.g., breast and endometrial cancer), Turner's syndrome, benign prostate hyperplasia (i.e., prostate enlargement), prostate cancer, elevated cholesterol, restenosis, endometriosis, uterine fribroid disease, hot flashes, and skin and/or vagina atrophy. Other estrogen receptor-mediated conditions that may be treated include neurological diseases and disorders including memory loss and dementia, and neurodegenerative disease, including Alzheimer's disease.

In addition to the potential beneficial effects of estrogen on episodic memory, some evidence suggests that HT reduced the risks of both dementia (including AD) and mild cognitive impairment (MCI). MCI is a condition thought to represent a transitional state between normal cognition and dementia in some individuals, with a 12% conversion rate from MCI to dementia each year. Observational studies repeatedly document that women taking HT enjoy an 30% reduced risk for dementia compared with women not taking HT [odds ratio range, 0.306 (Yaffe et al., 1998 JAMA 279:688; Hogervorst et al., 2003 Cochrane Database Syst Rev CD003122)]. Thus, observational studies suggest that declining reproductive function could be a modifiable risk factor for dementia or that HT/ET could serve a protective role against some of the risks for developing dementia.

Several recent observational studies have identified that the stage of reproductive aging at which HT/ET is started modifies the risk of dementia. In these studies, women who take HT/ET during the late menopause transition or early postmenopause have a lower risk of dementia than those starting HT/ET later (Zandi et al., 2002 JAMA 288:21239; Henderson et al., J Neurol Neurosurg Psychiatry 76:103 2005). Thus, the timing of starting HT/ET relative to the menopause has been proposed to be one factor explaining the otherwise discordant observations between the observational studies and the RCTs (Resnick and Henderson, 2002 JAMA 288:21702; Manson et al., 2006 Menopause 13:139). Recent preclinical studies reviewed below highlight the importance of timing of ET in this report.

Successful treatment of a subject may result in the prevention, inducement of a reduction in, or alleviation of symptoms in a subject afflicted with an estrogen receptor-mediated medical or biological disorder. Thus, for example, treatment can result in a reduction in breast or endometrial tumors and/or various clinical markers associated with such cancers. Treatment of Alzheimer's disease can result in a reduction in rate of disease progression, detected, for example, by measuring a reduction in the rate of increase of dementia.

Historically, there has been a presumption that declining reproductive function plays no role in the onset of mood disorders that occur during midlife in women. The symptoms of depression during the menopause transition also were assumed to be transient and of such minor severity that they were dismissed to be of little clinical consequence. Recent studies, however, suggest that these presumptions are incorrect. First, several community-based longitudinal studies have reported the relative independence of depressions during the menopause transition and hot flushes: both occur at this stage of life, but depression is not simply caused by hot flushes (Avis et al., 2001 Soc Sci Med 52:345). Second, recent longitudinal studies that followed women with no past history of depression demonstrated an increased risk of first-onset depressions during the late menopause transition (Schmidt et al., 2004 Am J Psychiatry 161:22384; Cohen et al., 2006 Arch Gen Psychiatry 63:385; Freeman et at, 2006 Arch Gen Psychiatry 61:62). Finally, both major and minor depressions are clinically significant to women at midlife, because both are associated with an increased risk for several other medical conditions (Wassertheil-Smoller et al., 2004 Arch Intern Med 164:289) relevant to the health of women at midlife (e.g., cardiovascular disease, dementia, and the metabolic syndrome).

The majority of women do not develop depression during the menopause transition, and, therefore, reproductive aging is not uniformly associated with either depressive symptoms or the syndrome of depression. Nonetheless, despite numerous studies concluding that the menopause is not associated with an increased risk for developing depression in women, several other longitudinal, community-based studies reported an association between the menopause transition and an increased risk for depression (Schmidt, 2005 Am J Med 118: 54). Indeed, five recent longitudinal studies all have documented an increased risk for depression during the menopause transition, with odds ratios ranging from 1.8 to 2.9 compared with the premenopause (Bromberger et al., 2001 Am J Public Health 91:14352; Freeman et al., 2004 Arch Gen Psychiatry 61:62, 2006 Arch Gen Psychiatry 63:375; Schmidt et al., 2004 Am J Psychiatry 161:22384; Cohen et al., 2006 Arch Gen Psychiatry 63:385). These data suggest that events surrounding the final menstrual period may predispose some women to develop clinically significant depressive illness. Although several factors could precipitate depression in these women, endocrine events are suggested by the stage of the menopause transition (i.e., late) during which depressions appeared. The late transition is characterized by more prolonged hypogonadism than the early perimenopause, during which estradiol secretion may be increased. Thus, the timing of appearance of the depressions observed suggest an endocrine mechanism related to the perimenopause (estradiol withdrawal and/or recent-onset of prolonged hypogonadism) in the pathophysiology of perimenopausal depression.

Efforts to investigate the potential role of declining ovarian hormone secretion in the onset of depression have examined the effects on mood of administering HT/ET in women with perimenopausal and postmenopausal depression. The antidepressant efficacy of estradiol has been examined in three relatively recent RCTs of women meeting standardized diagnostic criteria for major and minor depression, who were randomly assigned to enter double-blind, placebo-controlled trials (Schmidt et al., 2000; Soares et al., 2001 Arch Gen Psychiatry 58:529; Morrison et al., 2004 Biol. Psychiatry 55:406). In perimenopausal women, short-term administration (3 weeks) of estradiol significantly decreased depression scores compared with both baseline and placebo conditions. In one study, a full or partial therapeutic response was seen in 80% of perimenopausal women on estradiol compared with 22% of those on placebo (Schmidt et al., 2000). The efficacy of ET in perimenopausal depression is consistent with the observed effect size (0.69) in a recent meta-analysis of studies examining the effects of estrogen on mood (Zweifel and O'Brien, 1997 Psychoneuroendocrinology 22:189). The therapeutic response to estradiol was observed in both major and minor depression as well as in women with and without hot flushes. Thus, the efficacy of ET in perimenopausal depression is not solely a product of its ability to reduce the distress of hot flushes. In contrast to these studies in perimenopausal depression, the administration of estradiol under similar conditions failed to improve mood in depressed women who were 5 years postmenopause (Morrison et al., 2004). Thus, the effects of estradiol on depression may be limited to perimenopausal women. Additionally, as with the potential effects of estrogen on the course of dementia, the stage of reproductive aging at which women present and/or commence ET might modify the observed outcomes.

In summary, the majority of women do not develop depression during or after the menopause transition. Nevertheless, recent prospective studies monitoring both reproductive status and mood have documented that, for some women, perimenopause-related events increase the risk for the onset of depression. The role of ovarian function in these episodes of depression is suggested by both the timing of their onset relative to the last menstrual period and the antidepressant efficacy of short-term ET.

The amount of active ingredient that may be combined with the carrier materials to produce a single dosage form will vary depending upon the estrogen-mediated disease, the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The prophylactically or therapeutically effective amount for a given situation can be readily determined by routine experimentation and is within the skill and judgment of the ordinary clinician.

For exemplary purposes, a prophylactically or therapeutically effective dose will generally be from about 0.01 mg/kg/day to about 100 mg/kg/day, preferably from about 0.1 mg/kg/day to about 20 mg/kg/day, and most preferably from about 1 mg/kg/day to about 10 mg/kg/day of a estrogen receptor modulating compound, which may be administered in one or multiple doses.

IV. Kits

Kits may be provided which contain the formulation to be administered. The formulation may be administered once a day or more than once a day. The formulation can be administered enterally, parenterally, or topically. The kits typically contain the active agent(s) to be administered, excipients and carriers, and instructions for administration of the formulation. The kits may also contain equipment/devices used to administer the formulation, such as syringes.

The present invention will be further understood by reference to the following non-limiting examples.

EXAMPLES

Example 1

Identification of PhytoSERMS

ERβ has been associated with estrogen-induced promotion of memory function and neuronal survival. Based on the optimized complex structure of human ERβ LBD bound with genistein, computer-aided structure-based virtual screening against a natural source chemical database was conducted to determine the occurrence of plant-based ERβ-selective ligands. Twelve representative hits derived from database screening were assessed for their binding profiles to both ERs, three of which displayed over 100-fold binding selectivity to ERβ over ERα.

Materials and Methods

Identification of Molecules

Identification of Compounds in Database

All computational work was performed on a SOT Octane workstation equipped with the IRIX 6.5 operating system (Silicon Graphic Inc.). First, the 3D crystallographic structure of human ERβ LBD complexed with genistein was downloaded from the Protein Data Bank (PDB ID: 1QKM). The complex structure was fixed and energy minimized with the Accelrys molecular modeling software package InsightII 2000 (Accelrys Inc.). An in-house 2D natural source chemical collection containing approximately 25 000 plant-based natural molecules or derivatives was converted to a 3D multiconformational database with the Accelrys modeling software package Catalyst 9.8 (Accelrys Inc.).

The receptor-docking site was defined based on the binding position of genistein in the receptor and specified as all atoms within 10 Å of the center carbon of genistein. GOLD 2.0 (Genetic Optimization for Ligand Docking), an automated ligand docking program distributed by CCDC (Cambridge Crystallographic Data Center), was applied to calculate and rank the molecules based on their complementarities with the receptor binding site, on both geometrical and chemical features.

Prior to the database screening, initial validation using genistein as the test ligand was conducted. The aim of the validation test was to evaluate the effectiveness of the algorithm of the docking program in identifying the experimentally observed binding mode of the ligand in the receptor, to determine whether the program is applicable to the specific target system in this study. In addition, the validation test was used to determine the optimal parameter settings for the later database screening. Twenty docking runs were carried out on the test complex, using the fastest default generic algorithm parameters optimized for virtual library screening, and the GoldScore fitness function was applied. The validation test demonstrated that, based on the specified parameter settings, GOLD was effective in capturing the contributive hydrogen bond donor (ND1 in His 475) crucial to the binding and reproducing the nearly coincident solution in terms of both the binding orientation and conformation of genistein as observed in the experimental measurement (see FIG. 1). The root-mean-square (RMS) deviations were computed between the observed experimental position and the GOLD solutions, with RMSD 0.3299 and 0.4483 compared to top-ranked and worst solutions, respectively. The average RMSD of all solutions was 03566, which is regarded as a good prediction based on the subjective classifications defined by the program developer (refer to the program manual), suggesting that this program is reliable and applicable to the database screening toward ERβ.

Using the parameter settings determined in the validation test, the 3D natural source chemical database was input and docked into the prepared ERβ binding site in a flexible docking manner (full ligand and partial protein) and scored based on the GoldScore fitness function. Five hundred resultant top-scoring molecules were filtered via visual screening in the context of the receptor in InsightII. Based on visual analysis, 100 molecules underwent further analysis by Affinity, a more complex and predictive ligand docking program to refine the binding modes predicted by GOLD. The criteria used for the selection of candidate molecules for investigation included the following (a) formation of hydrogen bond with donor atom ND1 in His 475; (b) hydrophobic and hydrophilic balance appearing in the structure (e.g., the molecule should potentially have two relatively hydrophilic sides and a hydrophobic center to enhance both the steric and electrostatic complementarity with the receptor); (c) bound pose of the molecule in the receptor; and d) structural diversity. Finally, molecules that met the above criteria were computationally predicted for their drug-likeness (Lipinski's Rule of Five) and blood-brain barrier (BBB) penetration properties.

The ligand binding domains of the human ERα and ERβ are approximately 60% homologous. Structural modeling and mutational analyses indicate that two variant amino acid residues along the ligand binding pocket, Leu 384 and Met 421 in ERα, which are replaced with Met 336 and Ile 373, respectively, in ERβ, are the key molecular constituents underlying discriminative binding of selective ligands to either receptor subtypes. Sun, et al. *Mol. Endocrinol.* 2003, 17, 247-258. This slight structural variance serves as the foundation for both design and discovery of ER specific ligands. The similarities in the chemical features of both pairs of residues presents a substantial challenge to discover a selective ligand based on this difference. Of the known natural source ERβ-selective ligands, genistein remains the most selective. However, an increasing number of synthetic compounds are emerging showing greater selectivity than genistein for ERβ, as evidenced by the compound DPN developed in Katzellenebogen's laboratory. Computer-aided structure-based virtual database screening provides an efficient approach to rationally highlight a small group of lead candidates from a large number of compounds for investigation at the bench.

Determination of Binding Affinity and Selectivity

The binding affinity and selectivity of candidate molecules yielded from database screening were determined by a fluorescent polarization competitive binding assay using purified baculovirus-expressed human ERβ or ERα and a fluorescent estrogen ligand EL Red (PanVera Corp.). Test molecules were serially diluted to a 2× concentration in assay buffer (200 µM to 200 pM). Fifty microliters of preincubated 2× complex of ERβ (30 nM) or ERβ (60 nM) and EL Red (2 nM) was added to each well in a 96-well Non-binding Surface black microplate (Corning Life Sciences) for a final volume of 100 µL. Negative controls containing ER and EL Red (equivalent to 0% inhibition) and positive controls containing only free EL Red (equivalent to 100% inhibition) were included. After a 2-h incubation period at room temperature, the polarization values were measured using a Tecan GENios Pro reader at 535 nm/590 nm excitation/emission and plotted against the logarithm of the test molecule concentration. $IC_{50}$ values (concentration of test molecule that displaces half of the EL Red from ER) were determined from the plot using a nonlinear least-squares analysis.

Results 31 molecules that can form a hydrogen bond with ND1 in His 475 were selected and grouped into three categories based upon the chemical features that favored both the van der Waals (VDW) contact (the number of the rings in the structure) and electrostatic interactions (the number of the hydrogen bonds) with the receptor. 10 molecules that have strong VDW interactions with the receptor, but without contributive hydrogen bonding, were grouped in Category IV. These molecules contain three or four five- or six-membered rings in their structures that could promote the hydrophobic interactions with the center of the receptor binding site as observed in endogenous estrogen 17β-estradiol that consists of four rings in its structure and binds to the estrogen receptor with a high affinity.

Table 1 summarizes the $IC_{50}$ binding results of test molecules to both ERα and ERβ as well as the binding selectivity of representative molecules selected from four categories.

TABLE 1

Binding Affinity ($IC_{50}$) and Selectivity of Representative Molecules for Estrogen Receptor α and β

| Compd | Structure | $IC_{50}$ ERα | $IC_{50}$ ERβ | Selectivity (ERα/ERβ) |
|---|---|---|---|---|
| Progesteron | 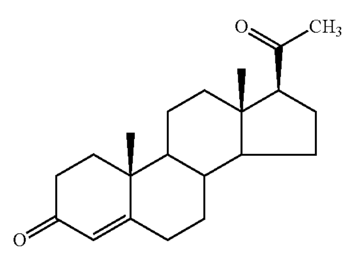 [SMILES: CC(=O)[C@H]1CCC2C3CCC4=CC(=O)CC[C@]4(C)C3CC[C@@]21C] | NC* | NC | |
| genistein | 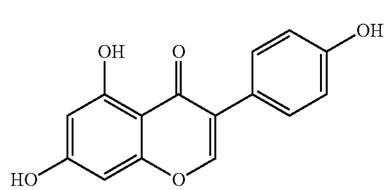 [SMILES: O=c1c(-c2ccc(O)cc2)coc2cc(O)cc(O)c12] | 4.68 µM | 98.7 nM | 47.2 |

TABLE 1-continued

Binding Affinity (IC$_{50}$) and Selectivity of
Representative Molecules for Estrogen Receptor α and β

| Compd | Structure | IC$_{50}$ ERα | IC$_{50}$ ERβ | Selectivity (ERα/ERβ) |
|---|---|---|---|---|
| 1 | 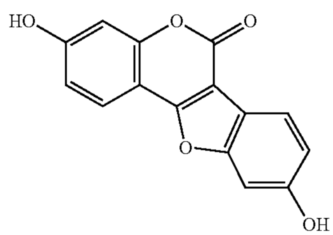 [SMILES: O=c1oc2cc(O)ccc2c2oc3cc(O)ccc3c12] | 75.7 nM | 18.6 nM | 4.07 |
| 2 | 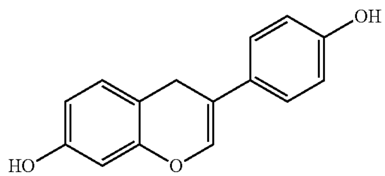 [SMILES: Oc1ccc(C2=COc3cc(O)ccc3C2)cc1] | NC | 0.68 μM | >100 |
| 3 | 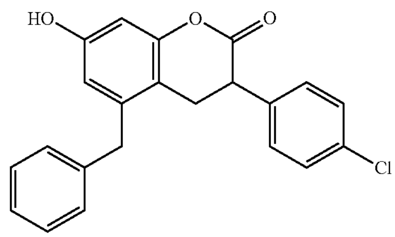 [SMILES: O=C1Oc2cc(O)cc(Cc3ccccc3)c2CC1c1ccc(Cl)cc1] | 120 nM | 250 nM | 0.48 |
| 4 | 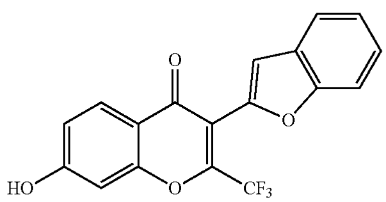 [SMILES: O=c1c(-c2cc3ccccc3o2)c(C(F)(F)F)oc2cc(O)ccc12] | NC | NC | |
| 5 | 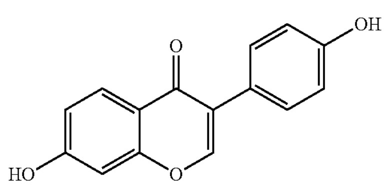 [SMILES: O=c1c(-c2ccc(O)cc2)coc2cc(O)ccc12] | NC | 2.80 μM | >100 |
| 6 | 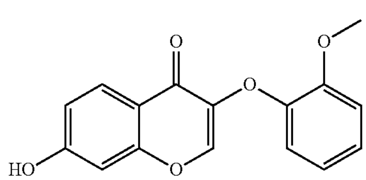 [SMILES: COc1ccccc1Oc1coc2cc(O)ccc2c1=O] | NC | NC | |
| 7 | 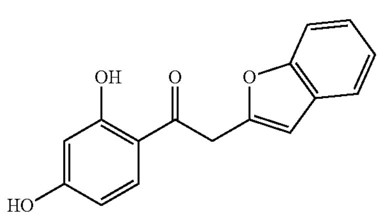 [SMILES: O=C(Cc1cc2ccccc2o1)c1ccc(O)cc1O] | 85.7 μM | 43.0 μM | 1.99 |

TABLE 1-continued

Binding Affinity (IC$_{50}$) and Selectivity of
Representative Molecules for Estrogen Receptor α and β

| Compd | Structure | IC$_{50}$ ERα | IC$_{50}$ ERβ | Selectivity (ERα/ERβ) |
|---|---|---|---|---|
| 8 | [structure] | NC | 4.48 μM | >100 |
| 9 | [structure] | NC | NC | |
| 10 | [structure] | NC | NC | |
| 11 | [structure] | 2.32 μM | NC | <0.01 |
| 12 | [structure] | NC | NC | |

*NC: Nonconvergence within the dose range, predicting that either the molecule does not bind to the receptor or that the binding affinity is very low, with an IC$_{50}$ greater than 1 mM.

As expected, the negative control steroid, progesterone, does not bind to either ER. As a positive natural source estrogen control, genistein was found to bind to ERβ with a 47.2-fold greater binding selectivity over ERα, but at an affinity one-fourth of 17β-estradiol. Among 12 molecules tested, five molecules, 1, 2, 5, 7, and 8, showed binding selectivity to ERβ over ERα, 3 of which, 2, 5, and 8, displayed the selectivity over 100-fold. Preliminary structure and binding activity relationship analyses revealed that both the central hydrophobic skeletal structure and the connected two polar 'arms' contribute to the binding affinity of ligands to both ERs. The enhanced VDW contact derives mainly from the central hydrophobic feature of the molecule. For example, the number of rings increases the binding affinity of molecules to the receptor, as indicated by the VDW value of 17β-estradiol (−67.98) versus that of genistein (−60.75) and molecule 9 (−58.04), which are well correlated with their order-different binding affinities. Meanwhile, the hydrogen bonds derived from the two polar "arms" of the molecule are essential for the binding as well. The lack of one "arm" of the hydrogen bond, as represented by molecule 4 and 6, or two 'arms', as represented by 10 and 12, even though the latter two molecules can elicit strong VDW interactions with the receptor, with the VDW value of −72.58 and −69.19, respectively, leads to either very weak or no binding. With respect to the binding selectivity, as demonstrated in the modeling complex structures of a synthetic ERβ-selective agonist, PPT, Stauffer, et al. *J. Med. Chem.* 2000, 43, 4934-4947 and a synthetic ERβ-selective agonist, DPN, Meyers, et al., *J. Med. Chem.* 2001, 44, 4230-4251, with both ERs, Zhao, et al. 2004 *Abstract Book*; The Keystone Symposia: Nuclear Receptors: Steroid Sisters, Keystone, Colo.; February 2004, relatively larger molecular size favors the binding selectivity for ERβ over ERα, as represented by molecule 3 and 11.

These analyses shed light on the future search and design of more active and selective ER subtype-selective ligands. Further, 3 out of 12 representative molecules yielded from database searching displayed over 100-fold selectivity toward ERβ over ERα, demonstrating the effectiveness of this computer-aided virtual screening approach applied in the present study in the discovery of potential molecules that preferentially interact with ERβ.

Example 2

Preclinical Identification of ERβ-Selective PhytoSERM Combinations for Prevention of Neurodegeneration The impact of ERb-selective PhytoSERMs when administered singly or in combination on neuronal survival and molecular/functional markers associated with prevention of neurodegeneration and Alzheimer's disease (AD) was investigated.

Materials and Methods

17β-Estradiol was purchased from Steraloids (Newport, R.I.). Genistein, daidzein and equol were purchased from Indofine Chemical (Hillsborough, N.J.). IBSO03569 was purchased from InterBioScreen (Moscow, Russia). The structures of these compounds are shown in FIG. 1.

In Vitro Treatments: Test compounds (or combinations) were first dissolved in analytically pure DMSO (10 mM) and diluted in Neurobasal medium to the working concentrations right before treatments.

In Vivo Treatments: Test compounds (or combinations) were first dissolved in analytically pure DMSO and diluted in corn oil (50 ml of DMSO in 950 ml of corn oil) to the working concentrations at 100 mg/ml for 17β-estradiol and 10 mg/ml for phytoSERMs.

In vitro Assays

ERα Binding Assays

ERα receptor (about 0.2 mg/ml, Affinity Bioreagents) is diluted to about $2\times10^3$ mg/ml in phosphate-buffered saline ("PBS") at a pH of 7.4. Fifty microliters of the EPα-PBS solution is then added to each of the wells of a flashplate. The plates are sealed and stored in the dark at 4° C. for 16-18 hours. The buffered receptor solution is removed just prior to use, and the plates are washed 3 times with 200 microliters per well of PBS. The washing is typically performed using a slow dispense of reagent into the wells to avoid stripping the receptor from the well surface.

For library screening, 150 microliters of 1 nM $^3$H-estradiol (New England Nuclear, Boston, Mass.) in 20 mM Tris-HCl, 1 mM EDTA, 10% glycerol, 6 mM monothioglycerol, 5 mM KCl, pH 7.8 is mixed with 50 microliters of the test compound (in same buffer) in a 96 well microtiter plate, resulting in a final estradiol concentration of 0.6 nM. In addition, several dilutions of estradiol, centered on the $IC_{50}$ of 1-2 nM, are also added to individual wells to generate a standard curve. The plates are gently shaken to mix the reagents. A total of 150 microliters from each of the wells is added to the corresponding wells of the pre-coated ERα plates. The plates are sealed and the components in the wells are incubated either at room temperature for 4 hours or at 4° C. overnight. The receptor bound ligand is read directly after incubation using a scintillation counter. The amount of receptor bound ligand is determined directly, i.e., without separation of bound from free ligand. If estimates of both bound and free ligand are required, the supernatant is removed from the wells, liquid scintillant is added, and the wells are counted separately in a liquid scintillation counter.

ERβ Binding Assays

ERβ receptor (.about.0.2 mg/ml, Affinity Bioreagents) is diluted to about $2\times10^3$ mg/ml in phosphate-buffered saline ("PBS") at a pH of 7.4. Fifty microliters of the ERβ-PBS solution is then added to each the wells of a flashplate. The plates are sealed and are stored in the dark at 4° C. for 16-18 hours. The buffered receptor solution is removed just prior to use, and the plates are washed 3 times with 200 microliters per well of PBS. The washing is typically performed using a slow dispense of reagent into the wells to avoid stripping the receptor from the well surface.

For library screening, 150 microliters of 1 nM $^3$H-estradiol (New England Nuclear, Boston, Mass.) in 20 mM Tris-HCl, 1 mM EDTA, 10% glycerol, 6 mM monothioglycerol, 5 mM KCl, pH 7.8 was mixed with 50 microliters of the test compound (in same buffer) in a 96 well microtiter plate, resulting in a final estradiol concentration of 0.6 nM. In addition, several dilutions of estradiol, centered on the $IC_{50}$ of 1-2 nM is also added to individual wells to generate a standard curve. The plates are then gently shaken to mix the reagents. A total of 150 microliters from each of the wells is added to the corresponding wells of the pre-coated ERβ plates. The plates are sealed and the components in the wells are incubated at room temperature either for 4 hours or at 4° C. overnight. The receptor bound ligand is read directly after incubation using a scintillation counter. The amount of receptor bound ligand is determined directly, i.e., without separation of bound from free ligand. If estimates of both bound and free ligand are required, the supernatant is removed from the wells, liquid scintillant is added, and the wells are counted separately in a liquid scintillation counter.

ERα/ERβ Transactivation Assays

Construction of Transfected CHO Cells

Transfected CHO cells were derived from CHO KI cells obtained from the American Type Culture Collection ("ATCC", Rockville, Md.): The transfected cells were modified to contain the following four plasmid vectors: (1) pKCRE with DNA for the human estrogen receptor, (2) pAG-60-neo with DNA for the protein leading to neomycin resistance, (3) pRO-LUC with DNA for the rat oxytocin promoter and for firefly luciferase protein, and (4) $pDR_2$ with DNA for the protein leading to hygromycine resistance. All transformations with these genetically modified CHO cells are performed under rec-VMT containment according to the guidelines of the COGEM (Commissie Genetische Modificatie). Screening is performed either in the absence of estradiol (estrogenicity) or in the presence of estradiol (anti-estrogenicity).

Assays to Assess Neuronal Function

Neuronal Culture Preparation

Primary cultures of hippocampal neurons were obtained from Embryonic Day 18 (E18d) rat fetuses. Briefly, after dissected from the brains of the rat fetuses, the hippocampi were treated with 0.02% trypsin in Hank's balanced salt solution (137 mM NaCl, 5.4 mM KCl, 0.4 mM $KH_2PO_4$, 0.34 mM $Na_2HPO_4.7H_2O$, 10 mM glucose, and 10 mM HEPES) for 5 min at 37° C. and dissociated by repeated passage through a series of fire-polished constricted Pasteur pipettes. Between $2\times10^4$ and $4\times10^4$ cells were plated onto poly-D-lysine (10 µg/ml)-coated 22 mm coverslips in covered 35 mm petri dishes for morphological analysis, and $1\times10^5$ cells/ml were plated onto poly-D-lysine-coated 24-well, 96-well culture plates or $3-5\times10^5$ cells/ml onto 0.1% polyethylenimine-coated 60 mm petri dishes for biochemical analyses. Nerve cells were grown in phenol-red free Neurobasal medium (NBM, Invitrogen Corporation, Carlsbad, Calif.) supplemented with B27, 5 U/ml penicillin, 5 µg/ml streptomycin, 0.5 mM glutamine and 25 µM glutamate at 37° C. in a humidified 10% $CO_2$ atmosphere at 37° C. for the first 3 days and NBM without glutamate afterwards. Cultures grown in serum-free Neurobasal medium yield approximately 99.5% neurons and 0.5% glial cells.

Neuroprotection Measurements
Glutamate Exposure

Primary hippocampal neurons were pretreated with compounds for 48 hr followed by exposure to 100 glutamate for 5 min at room temperature in HEPES buffer containing 100 mM NaCl, 2.0 mM KCl, 2.5 mM $CaCl_2$, 1.0 mM $MgSO_4$, 1.0 mM $NaH_2PO_4$, 4.2 mM $NaHCO_3$, 10.0 mM glucose and 12.5 mM T-LEPES. Immediately following glutamate exposure, cultures were washed once with HEPES buffer and replaced with fresh Neurobasal medium containing the test compounds. Cultures were returned to the culture incubator and allowed to incubate for 24 hr prior to cell viability measurements on the following day.

Western Immunoblotting
CREB Phosphorylation

Nuclear lysates were prepared as following: Briefly, hippocampal neurons grown on poly-D-lysine coated culture dishes were treated with compounds for appropriate periods, washed with cold PBS once and scraped into 1 ml PBS. Cells were then centrifuged at 5,000 rpm for 5 min, and the pellet was dissolved in Cytoplasm Extraction buffer (10 mM HEPES, 1 mM EDTA, 60 mM KCl, 0.075% Igepal and protease and phosphatase inhibitor cocktail) and suspended by passage through a 200 µl pipette tip. After 30-45 RPM of incubation at 4° C., the samples were centrifuged at 5,000 rpm for 5 min to generate the cytoplasmic extract in the supernatant. The supernatant cytoplasmic extract was removed, and Nuclear Extraction buffer (20 mM Tris HCl, 1.5 mM $MgCl_2$, 420 mM NaCl, 0.2 mM EDTA, 25% glycerol, 0.5% Igepal and protease and phosphatase inhibitor cocktail) was added to the pellet followed by 5 M NaCl to break the nuclear membrane. Following 30-45 RPM of incubation at 4° C., the samples were centrifuged at 12,000 rpm for 10 min to generate a supernatant containing the nuclear extract.

Protein concentration was determined by the BCA method. An appropriate volume of 2× sample buffer was added to the protein samples, and samples were boiled at 95° C. for 5 min. Samples (25 µg of proteins per well) were loaded on a 10% SDSPAGE gel and resolved by standard electrophoresis at 90V, Proteins were then electrophoretically transferred to Immobilon-P PVDF membranes overnight at 32 V at 4° C. Membranes were blocked for 1 hr at room temperature in 10% non-fat dried milk in PBS containing 0.05% Tween 20 (PBS-T), incubated with appropriate primary antibodies against phospho-CREB (pSER[133], mouse monoclonal, 1:2000; Cell Signaling Technology, Beverly, Mass.), CREB (rabbit polyclonal, 1:1000; Cell Signaling Technology, Beverly, Mass.), spinophilin (rabbit polyclonal, 1:1000; Upstate Biotechology, Lake Placid, N.Y.), actin (mouse monoclonal, 1:1000; Santa Cruz Biotechnology, Inc., Santa Cruz, Calif.) or histone H1 (mouse monoclonol, 1:250; Santa Cruz Biotechology, Inc., Santa Cruz, Calif.) at temperatures and times specified by the antibody providers. All primary antibodies were dissolved in PBS-T with 1% horse serum (for mouse monoclonal antibody) or goat serum (for rabbit polyclonal). After washing in PBS-T, the membranes were incubated with horseradish peroxidase-conjugated anti-mouse IgG (1:5000; Vector Laboratories, Inc., Burlingame, Calif.) in PBS-T with 1% horse serum or anti-rabbit IgG (1:5000; Vector Laboratories, Inc., Burlingame, Calif.) in PBS-T with 1% goat serum for 1 hr. Immunoreactive bands were visualized by TMI3 detection kit (Vector Laboratories. Inc., Burlingame, Calif.) and quantified using Un-Scan-It gel image software (Silk Scientific, Inc., Orem, Utah). Following transfer, gels were stained with Coomassie blue (Bio-rad Laboratories, Hercules, Calif.) to ensure equal protein loading.

Bcl-2 and Bcl-xl Expression

Primary hippocampal neurons were pretreated with compounds for 48 hr before the cells were lysed by incubation in ice-cold lysis buffer containing: 0.005% SDS, 0.1% Igepal, 0.2 mM sodium orthovanadate, 0.2 mM phenylmethylsulfonylfluoride and protease inhibitor mixture in PBS at 4° C. for 45 min. Cell lysates were centrifuged at 10,000 rpm at 4° C. for 10 min, and the concentration of protein in the supernatant was determined using the BCA Protein Assay (Pierce Biotechnology, Inc., Rockford, Ill.). 25 µg of total protein were diluted in 15 µl 2×SDS containing sample buffer and the final volume was made 30 µl with water. After denaturalization on a hot plate at 95-100° C. for 5 min, 25 µl of the mixture were loaded per lane on 10% SDS-polyacrylamide mini-gels followed by electrophoresis at 90V. The proteins were then electro-transferred to polyvinylidene difluoride membranes (Millipore Corp., Bedford, Mass.) from the gels, Nonspecific binding sites were blocked with 5% nonfat dry milk in PBS containing 0.05% Tween™-20 (PBS-Tween™). Membranes were incubated with the primary monoclonal antibody against Bcl-2 (Zymed Laboratories, Inc., S. San Francisco, Calif.) diluted 1:250 in PBS-Tween ™with 1% horse serum (Vector Laboratories, Inc., Burlingame, Calif.) overnight at 4° C., then incubated with the secondary horseradish peroxidase (HRP)-conjugated horse anti-mouse IgG (Vector Laboratories, Inc, Burlingame, Calif.) diluted 1:5,000 in PBS-Tween™ with 1% horse serum for 2 hr at room temperature, and Bcl-2 proteins were visualized by developing the membranes with TAB substrate for peroxidase (Vector Laboratories, Inc., Burlingame, Calif.). β-Actin (Santa Cruz Biotechnology, Inc., Santa Cruz, Calif.) level was determined to ensure equal protein loading, and high-range Precision Protein Standards (Bio-Rad Laboratories, Hercules, Calif.) was used to determine protein sizes. Relative intensities of bands were quantified by optical density analysis using an image digitizing software Un-Scan-Tt version 5.1 (Silk Scientific, Inc., Orem, Utah).

Statistics

Statistically significant differences between groups were determined by a one way analysis of variance (ANOVA) followed by a Newman-Keuls post hoc analysis.

In vivo Assays
Immature Rat Uterotrophic Bioassay for Estrogenicity Anti-Estrogenicity Antiestrogenic activity was determined by the ability of a test compound to suppress the increase in uterine wet weight resulting from the administration of 0.2 µg 17-β-estradiol ("$E_2$") per day. Any statistically significant decreases in uterine weight in a particular dose group as compared with the $E_2$ control group are indicative of anti-estrogenicity.

One hundred forty (140) female pups (19 day s old) in the 35-50 g body weight range are selected for the study. On day 19 of age, when the pups weigh approximately 35-50 g, they are body weight-order randomized into treatment pups. Observations for mortality, morbidity, availability of food and water, general appearance and signs of toxicity are made twice daily. Pups not used in the study are euthanized along with, the foster dams. Initial body weights are taken just prior to the start of treatment at day 19 of age. The final body weights are taken at necropsy on day 22 of age.

Treatment commences on day 19 of age and continues until day 20 and 21 of age. Each animal is given three subcutaneous ("sc") injections daily for 3 consecutive days. Three rats in each of the control and mid- to high-level dose test groups are anesthetized with a ketamine/xylazine mixture. Their blood is collected by exsanguination using a 22 gauge needle and 5 ml syringe flushed with 10 USP with sodium heparin/ml through the descending vena cava; and then transferred into a 5 ml green top plasma tube (sodium heparin (freeze-dried), 72 USP units). Plasma samples are collected by centrifugation, frozen at −70° C., and analyzed using mass spectrographic to determine the presence and amount of test compound in the serum. Blood chemistry is also analyzed to determine other blood parameters. The uteri from the rats are excised and weighed. The remaining rats are sacrificed by asphyxiation under $CO_2$. The uteri from these rats are excised, nicked, blotted to remove fluid, and weighed to the nearest 0.1 mg.

In order to determine whether the test compound significantly affected final body weight, a parametric one-way analysis of variance (ANOVA) is performed (SIGMASTAT version 2.0, available commercially from Jandel Scientific, San Rafael, Calif.). Estrogen agonist and antagonist activity is assessed comparing uterine wet weights across treatment groups using a parametric ANOVA on loglo transformed data. The data are transformed to meet assumptions of normality and homogeneity of variance of the parametric AWQVA. The F value is determined and a Student-Newman-Kuels multiple range test is performed to determine the presence of significant differences among the treatment groups. The test compound is determined to act as a mixed estrogen agonist/antagonist if the test compound does not completely inhibit the 17-β-estradiol stimulated uterotrophic response.

The use of animals was approved by the Institutional Animal Care and Use Committee at the University of Southern California (Protocol Number: 10780). Embryonic day 18 Sprague-Dawley rat (Harlan, Indianapolis, Ind.) fetuses were used to obtain primary hippocampal neuronal cultures for in vitro experiments. Young adult (14 to 16-week-old, weighing from 270-290 g) female ovariectomized Sprague-Dawley rats (Harlan) were used for in vivo experiments.

In vitro neuroprotection and associated mechanistic studies were conducted in primary hippocampal neurons obtained from embryonic day 18 rat fetuses. Adult female ovariectomized rats were used to relate the in vitro findings to in vivo environment, along with the assessment of the impact of PhytoSERMs on brain mitochondrial functions and uterine weight.

During a 2-week surgery recovery following ovariectomy, but before treatment, rats were placed on a phytoSERM-reduced diet, TD.96155 (Harlan Teklad). Rats were given, once daily, 2 subcutaneous injections of vehicle (control), 17 β-estradiol (70 μg/kg BW), genistein (6 mg/kg BW), or phytoSERM combinations (6 mg/kg BW). Dosages used here are commensurate with those used in humans.

Following the second injection, animals fasted for 24 hours prior to sacrifice and brain dissection. Hippocampal and cortical tissues were collected from one hemisphere and stored for biochemical analyses. The remaining brain tissues minus cerebellum, pineal gland, and brainstem were utilized for mitochondrial isolations, followed immediately by mitochondria respiratory activity measurements. The rest of mitochondrial samples were stored for cytochrome c oxidase activity measurements. Uteri were excised, trimmed of fat and connective tissue, and both a wet weight and a dry weight were recorded.

Results

The PhytoSERMs tested are shown in FIG. 1.

Selective Binding for both ERβ and ERα

FIG. 2 presents the competition binding curves of four known ER ligands for both ERβ and ERα. The $IC_{50}$ determined for these ligands from the binding curves are consistent with the previously reported values using alternative methods such as radioligand assay, demonstrating the reliability of this assay in determining the binding profiles of small molecules to both ERs.

Figure 2A:
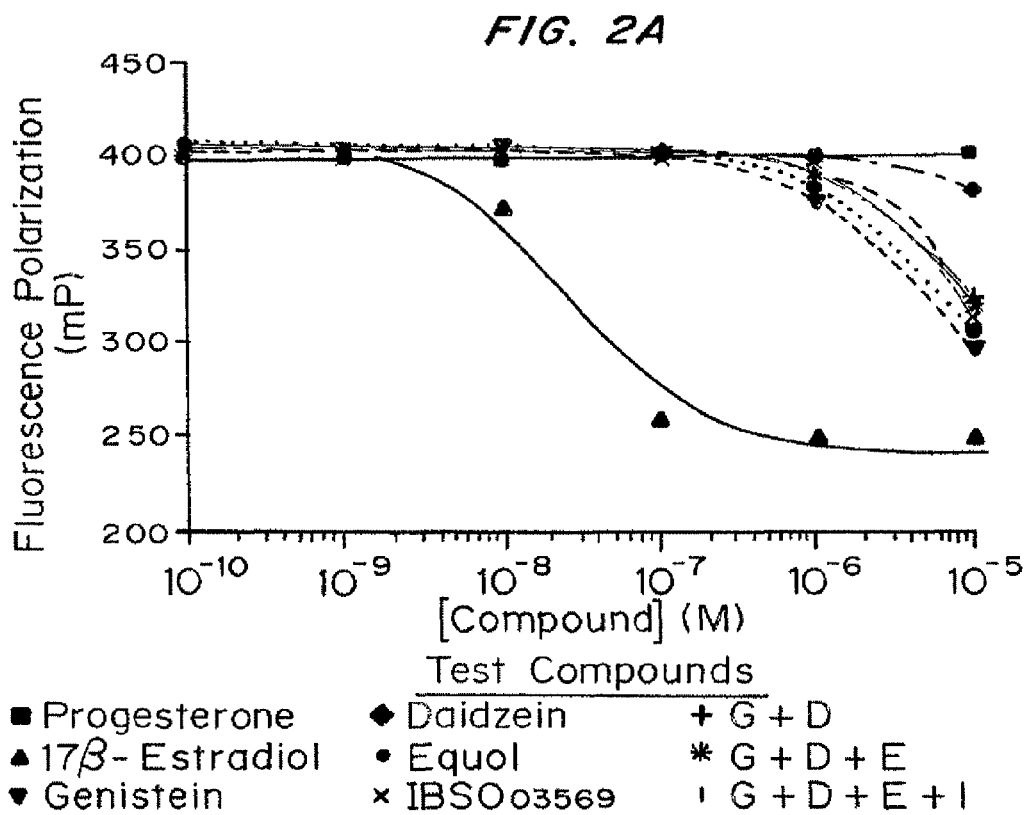
FIGS. 2A and 2B show the competition binding curves for ERα and ERβ (molar concentration versus fluorescence polarization (mP)) of G, D, E, I or combinations: G+D, G+D+E, or G+D+E+I.
Figure 2B:
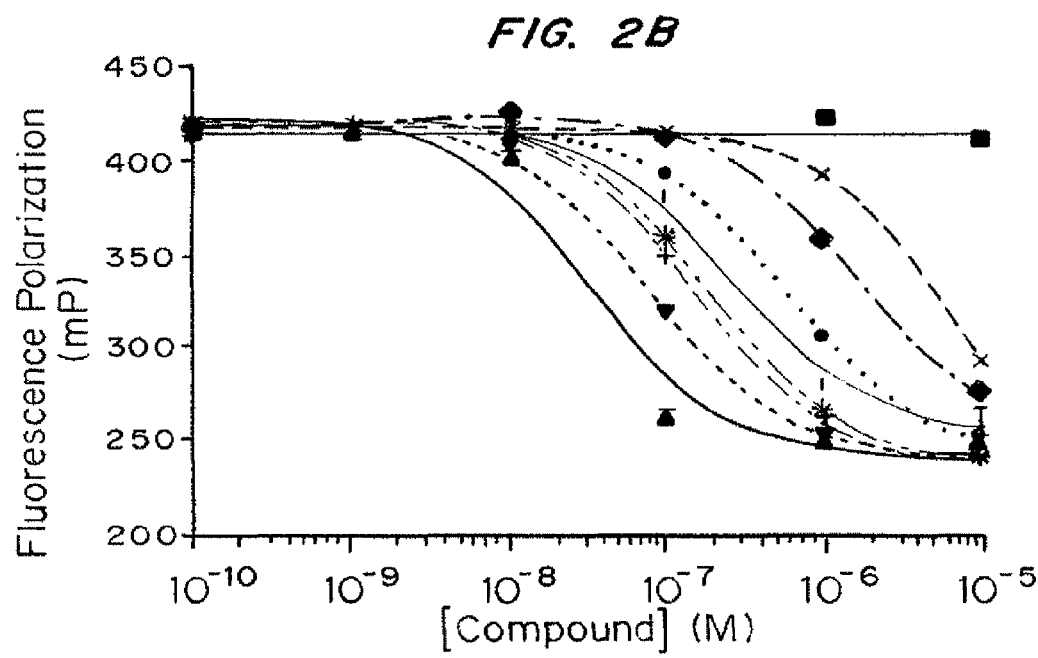

FIGS. 2A and 2B show the competition binding curves for ERα and ERR. Data were generated with a fluorescence polarization-based competitive binding assay using full-length human ERα and ERβ, and plotted against the logarithm of serially diluted concentrations of the test compounds (or combinations). Progesterone served as a negative control. 17β-Estradiol served as a positive control. Combined formulations were composed of equivalent molar of individual phytoSERMs included. G: genistein; D: daidzein; E: equol; I: IBSO03569. 17β-estradiol has no binding preference to ERα or to ERβ. The concentration of a test molecule resulting in the half-maximum shift in polarization value equals its $IC_{50}$. Non-convergence within the dose range, predicts that either the molecule does not bind to the receptor or that the binding affinity is very low.

Table 2 shows the binding data for ERα and ERβ.

TABLE 2

Binding data for ERα and ERβ

| Compounds | ERα | | | ERβ | | | Selectivity (β/α) |
| --- | --- | --- | --- | --- | --- | --- | --- |
| | $IC_{50}$ (μM) | RBA (%)[A] | $R^{2B}$ | $IC_{50}$ (μM) | RBA (%)[A] | $R^{2B}$ | |
| Progesterome | Non-Binding | | | Non-Binding | | | |
| 17β-Estradiol | 0.0253 | 100.0 | 0.9791 | 0.0325 | 100.0 | 0.9611 | 0.78 |
| Genistein | 4.735 | 0.5343 | 0.9811 | 0.0789 | 41.12 | 0.9908 | 60.0 |
| Daidzein | 26.65 | 0.0949 | 0.7876 | 1.738 | 1.867 | 0.9883 | 14.27 |
| Equol | 5.876 | 0.4306 | 0.9948 | 0.5825 | 5.571 | 0.9986 | 10.09 |
| IBSQ03569 | 1695 | 0.0015 | 0.9917 | 7.819 | 0.415 | 0.9959 | >100 |
| G + D | 9.896 | 0.2557 | 0.9865 | 0.1574 | 20.62 | 0.9970 | 52.57 |

TABLE 2-continued

Binding data for ERα and ERβ

| Compounds | ERα | | | ERβ | | | Selectivity (β/α) |
|---|---|---|---|---|---|---|---|
| | IC$_{50}$ (μM) | RBA (%)[A] | R[2B] | IC$_{50}$ (μM) | RBA (%)[A] | R[2B] | |
| G + D + E | 15.71 | 0.1610 | 0.9925 | 0.1902 | 17.06 | 0.9969 | 82.60 |
| G + D + E + I | 13.85 | 0.1596 | 0.9932 | 0.2615 | 12.41 | 0.9891 | 60.61 |

[A]RBA (%) refers to the relative binding affinity of the test compound (combination) that is expressed as the percent of the binding affinity of 17 β-estradiol (RBA = 100%).
[B]R² refers to goodness of fit of nonlinear regression between the binding curve and the data. Between 0.0 and 1.0, higher values indicate that the curve fits the data better. A fit with a R2 at 1.0 indicates that all points lie exactly on the curve with no scatter.

Neuroprotective Effect

Figure 3:
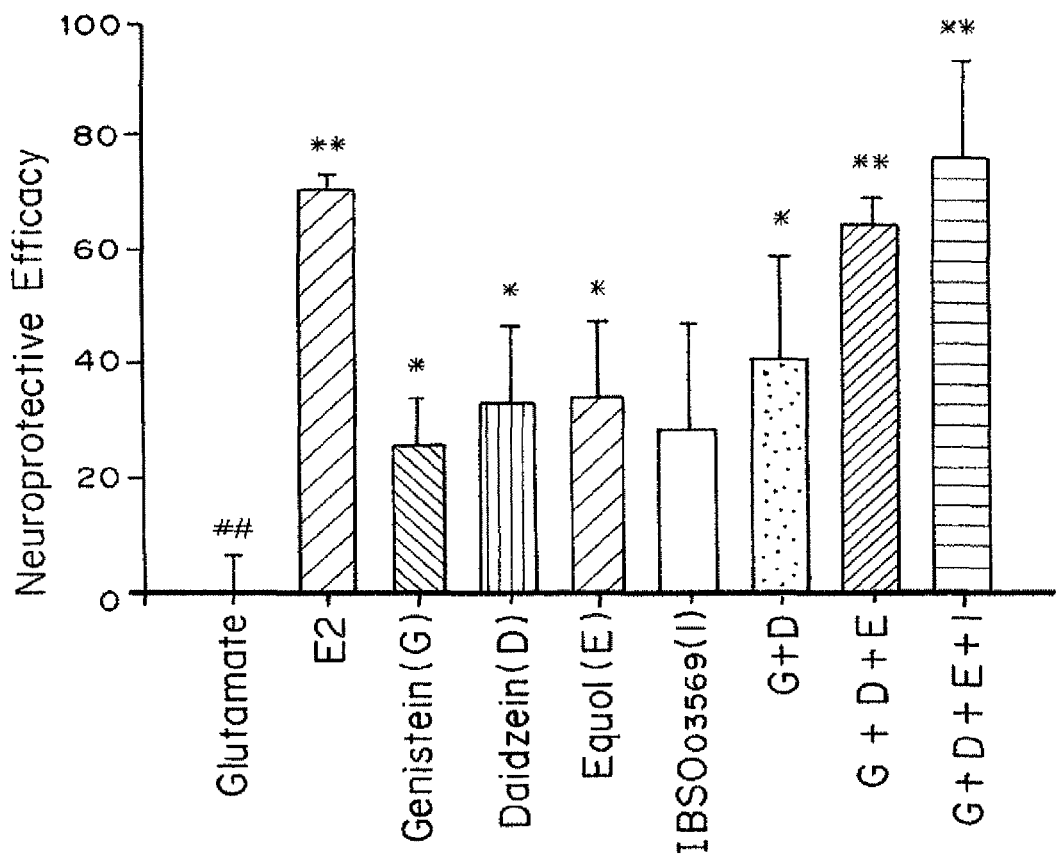
FIG. 3 is a graph showing the neuroprotective efficacy of four ERβ-selective phytoestrogenic molecules when administered alone at concentrations that elicited the maximal neuroprotective effects as revealed from the dose-response analyses (100 nM for all four molecules Genistein (G), Daidzein (D), Equol (E) and IBSO03569 (I)), or co-administered: G+D, G+D+E, or G+D+E+I, against supraphysiological glutamate (100 μM)-induced neurotoxicity primary hippocampal neurons by measurement of calcein AM staining.

Table 3 and FIG. 3 show the dose-dependent neuroprotective effects of four ERβ-selective phytoestrogenic molecules against supraphysiological glutamate (100 μM)-induced neurotoxicity in primary hippocampal neurons by measurement of LDH release. [##]P<0.01 compared to vehicle alone-treated cultures; * P<0.05 and ** P<0.01 compared to glutamate alone-treated cultures.

TABLE 3

Dose-dependent effects of individual phytoSERMs against glutamate-induced neurotoxicity in primary hippocampal neurons by LDH measurements[A]

| | LDH Release (% of Control) |
|---|---|
| Treatment_Genistein | |
| Control | 100.00 ± 3.09 |
| Glutamate alone | 410.99 ± 8.27[##] |
| 1 nM | 361.03 ± 7.71** |
| 10 nM | 350.02 ± 8.21** |
| 100 nM | 347.24 ± 16.96** |
| 1 μM | 356.79 ± 11.15** |
| 10 μM | 377.84 ± 8.45** |
| Treatment_Daidzein | |
| Control | 100.00 ± 4.28 |
| Glutamate alone | 378.26 ± 11.95[##] |
| 1 nM | 338.39 ± 16.49 |
| 10 nM | 333.98 ± 9.10* |
| 100 nM | 301.42 ± 7.70** |
| 1 μM | 318.49 ± 15.92** |
| 10 μM | 325.41 ± 26.12* |
| Treatment_Equol | |
| Control | 100.00 ± 14.95 |
| Glutamate alone | 460.27 ± 12.20[##] |
| 1 nM | 453.50 ± 23.37 |
| 10 nM | 403.78 ± 17.02* |
| 100 nM | 331.59 ± 9.67** |
| 1 μM | 381.80 ± 12.01** |
| 10 μM | 390.21 ± 9.40** |
| Treatment_IBSO03569 | |
| Control | 100.00 ± 2.05 |
| Glutamate alone | 281.17 ± 6.77[##] |
| 1 nM | 262.41 ± 10.60 |
| 10 nM | 270.86 ± 12.94 |
| 100 nM | 220.56 ± 6.80** |

TABLE 3-continued

Dose-dependent effects of individual phytoSERMs against glutamate-induced neurotoxicity in primary hippocampal neurons by LDH measurements[A]

| | LDH Release (% of Control) |
|---|---|
| 1 μM | 246.30 ± 7.70** |
| 10 μM | 307.53 ± 2.62 |

[A]Primary hippocampal neurons grown for 7 DIV were pretreated with the test phytoSERMs at serially diluted concentrations for 48 h, followed by a 5-min exposure to 100 mM glutamate. The amount of LDH released into the culture media was measured 24 h later.
[B]Data are derived from a single experiment and are representative of at lease three independent experiments. Results are presented as the percent of LDH release from vehicletreated control cultures and expressed as means ± S.E.M., n 6.
[##]P < 0.01 compared to vehicle-treated control cultures,
*P < 0.05 and
**P < 0.01 compared to glutamate alone-treated cultures; [#]P < 0.05 and [##]P < 0.01 compared to cultures treated with 10 nM phytoSERMs; [#]P < 0.05 and [##]P < 0.01 compared to cultures treated with 1 μM phytoSERMs; [#]P < 0.05 and [##]P < 0.01 compared to cultures treated with 10 mM phytoSERMs.

FIG. 3 shows the neuroprotective efficacy of four ERβ-selective phytoestrogenic molecules when administered alone at concentrations that elicited the maximal neuroprotective effects as revealed from the dose-response analyses (100 nM for all four molecules), or co-administered, against supraphysiological glutamate (100 μM)-induced neurotoxicity in primary hippocampal neurons by measurement of calcein AM staining. Results are presented in terms of neuroprotective efficacy $$NE = (V_{treatment} - V_{glutamate})/(V_{control} - V_{glutamate}) *100\%, \quad (1)$$

where $V_{treatment}$ is the individual value from phytoestrogen-treated cultures, $V_{glutamate}$ is a mean value from glutamate alone-treated cultures, and $V_{control}$ is a mean value from vehicle-treated control cultures. [##]P<0.01 compared to vehicle alone-treated cultures; * P<0.05 and **P<0.01 compared to glutamate alone-treated cultures.

Data presented in FIG. 3 and Table 3 demonstrate that although the four ERβ-selective phytoestrogenic molecules, when administered individually, are concentration-dependent and are protective against excitotoxic glutamate-induced neurotoxicity in primary neurons, these effects are moderate and arise from the weaker binding to the estrogen receptor compared to the endogenous estrogen 17β-estradiol (E2). FIG. 3 demonstrates that co-administration of 3 or 4 of these phytoestrogens afforded much greater neuroprotective efficacy compared to administration of single phytoestrogens or a combination of 2 phytoestrogens.

Expression of Anti-Apoptotic Proteins Bcl-2 and Bcl-xL

These outcomes are paralleled by the results derived from the western analyses of the expression of anti-apoptotic proteins, Bcl-2 and Bcl-xL, in primary neurons. FIGS. 4A-4B shows the effects on Bcl-2 and Bcl-XL expression in rat primary hippocampal neurons and hippocampal tissues derived from adult ovariectomized rats. Primary hippocampal neurons grown for 7 divisions were treated with the test compounds (or combinations) for 48 hr followed by Western blot analyses. Adult ovariectomized rats were given, once daily, 2 subcutaneous injections of the test compounds (or combinations). Rats were sacrificed 24 h later following the 2nd injection. Hippocampal tissues were homogenized followed by Western blot analyses. Combined formulations were composed of equivalent molar in (A) and equivalent weight in (B) of individual phytoSERMs including G: genistein; daidzein; E: equol; and I: IBSO003569.

Incubation of neurons with a combination of four phytoestrogens for 48 hours induces a significantly increased expression of both proteins comparable to those induced by E2. This is illustrated in FIG. 4, which shows the effect of four ERβ-selective phytoestrogenic molecules when co-administered (100 nM for all four molecules) on the expression of the anti-apoptotic proteins, Bcl-2 and Bcl-xL, in primary hippocampal neurons. **P<0.01 compared to vehicle alone-treated cultures. By comparison, a combination of two phytoestrogens is not sufficient to induce a significant increase in the expression of both proteins, as also illustrated in FIGS. 4A and 4B.

Up-regulation of the Bcl-2 family anti-apoptotic proteins have been associated with the neuroprotective mechanism elicited by E2. These data indicate that a combined used of multiple ERβ-selective phytoestrogens is effective to activate the neuroprotective mechanism leading to improved neuronal survival against neurodegenerative insults. Estrogen receptor interaction with p85/PI3K also enhances pAkt, which phosphorylates the proapoptotic protein Bcl-2-associated death protein (BAD) to prevent heterodimerization with, and inactivation of, Bcl-2. In cortical neurons, estradiol induced pAkt translocation to the nucleus. Recent analyses indicate that estradiol, via the PI3K signaling pathway, activates both the Akt and the ERK1/2 cascades in the same population of cortical and hippocampal neurons. Simultaneous activation of two pathways that prevent mitochondria from activating cell-death cascades is likely to promote neuron survival.

Increased Expression of the Anti-β-Amyloid Protein, IDE

Figure 5:
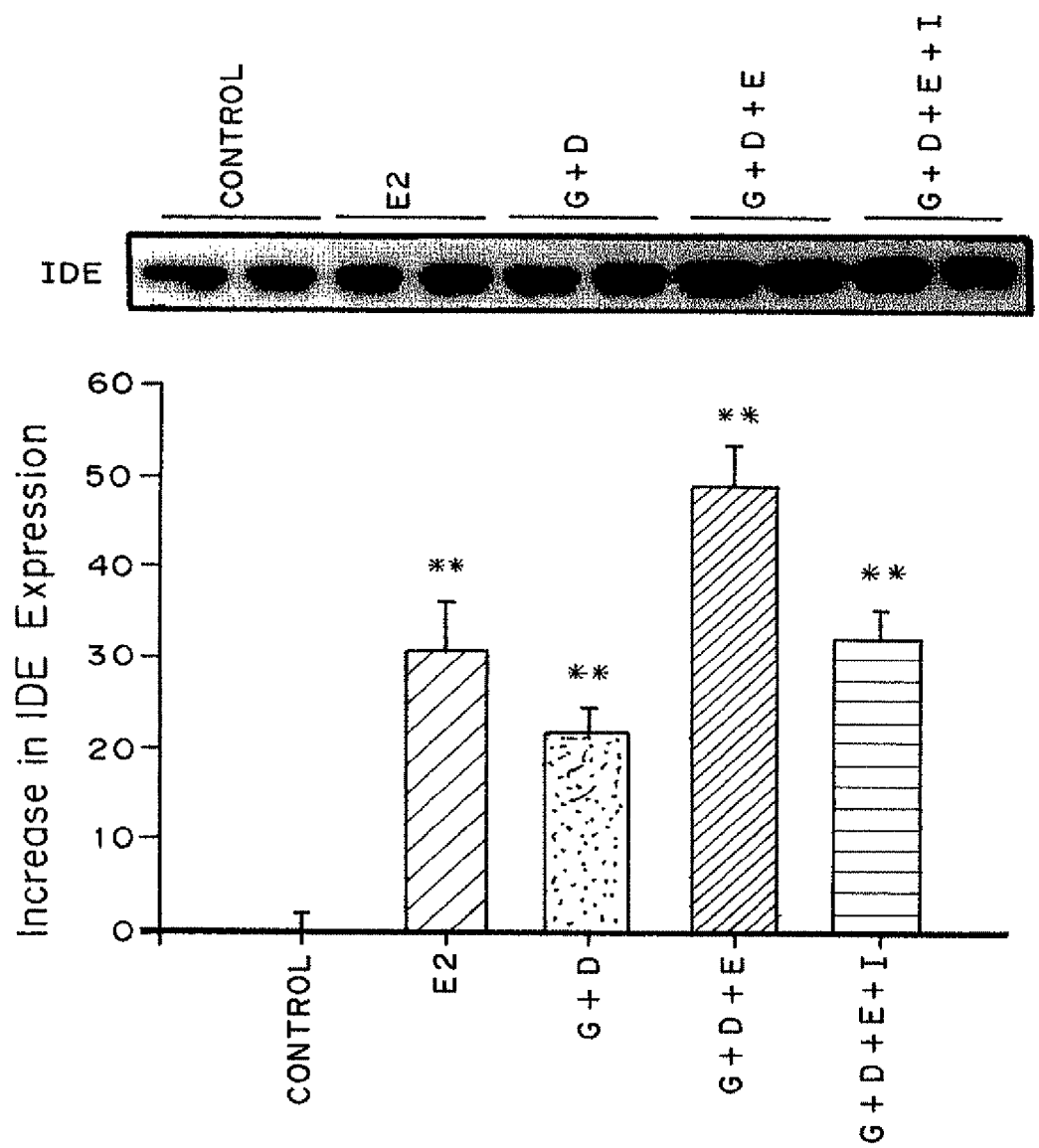
FIG. 5 is a graph illustrating the effect of four ERβ-selective phytoestrogenic molecules when co-administered (100 nM for all four molecules), G+D, G+D+E, or G+D+E+I, on the expression of the anti-β-amyloid protein, insulin-degrading enzyme ("IDE"), in primary hippocampal neurons.

FIG. 5 illustrates the effect of four ERβ-selective phytoestrogenic molecules when co-administered (100 nM for all four molecules) on the expression of the anti-β-amyloid protein, insulin-degrading enzyme ("IDE") in primary hippocampal neurons. **P<0.01 compared to vehicle alone-treated cultures. FIG. 5 demonstrates the effects of these various combinations of phytoestrogens along with E2 on the expression of the anti-β-amyloid (anti-Aβ) protein, insulin-degrading enzyme (IDE) in primary neurons. Data showed that all three combinations composed of two, three or four phytoestrogens significantly increases IDE expression in neurons. Among them, a combination of three phytoestrogens induced the greatest neuronal response, with an efficacy greater than E2 as well as a combination of two phytoestrogens.

It is clear that one neuropathological hallmark of AD is a significant deposition of extracellular Aβ peptide, as referred to Aβ plaque. Impaired Aβ clearance and/or degradation has been demonstrated to contribute in part to Aβ plaque formation in AD brain. Besides degrading insulin and several regulatory peptides, IDE, a metalloprotease enzyme, has been demonstrated to play a key role in degrading Aβ peptide monomer in the brain. Choronic upregulation of IDE represents a novel efficacious therapeutic approach to lowering the steady-state Aβ level in the brain and eventually preventing the occurrence of Alzheimer-type pathology. Therefore, these data indicate that coadministration of multiple ERβ-selective phytoestrogens have the potential to activate the anti-Aβ mechanism, and as a result, maintain the brain in a long-term healthy status.

Upregulation of Spinophilin

Figure 6:
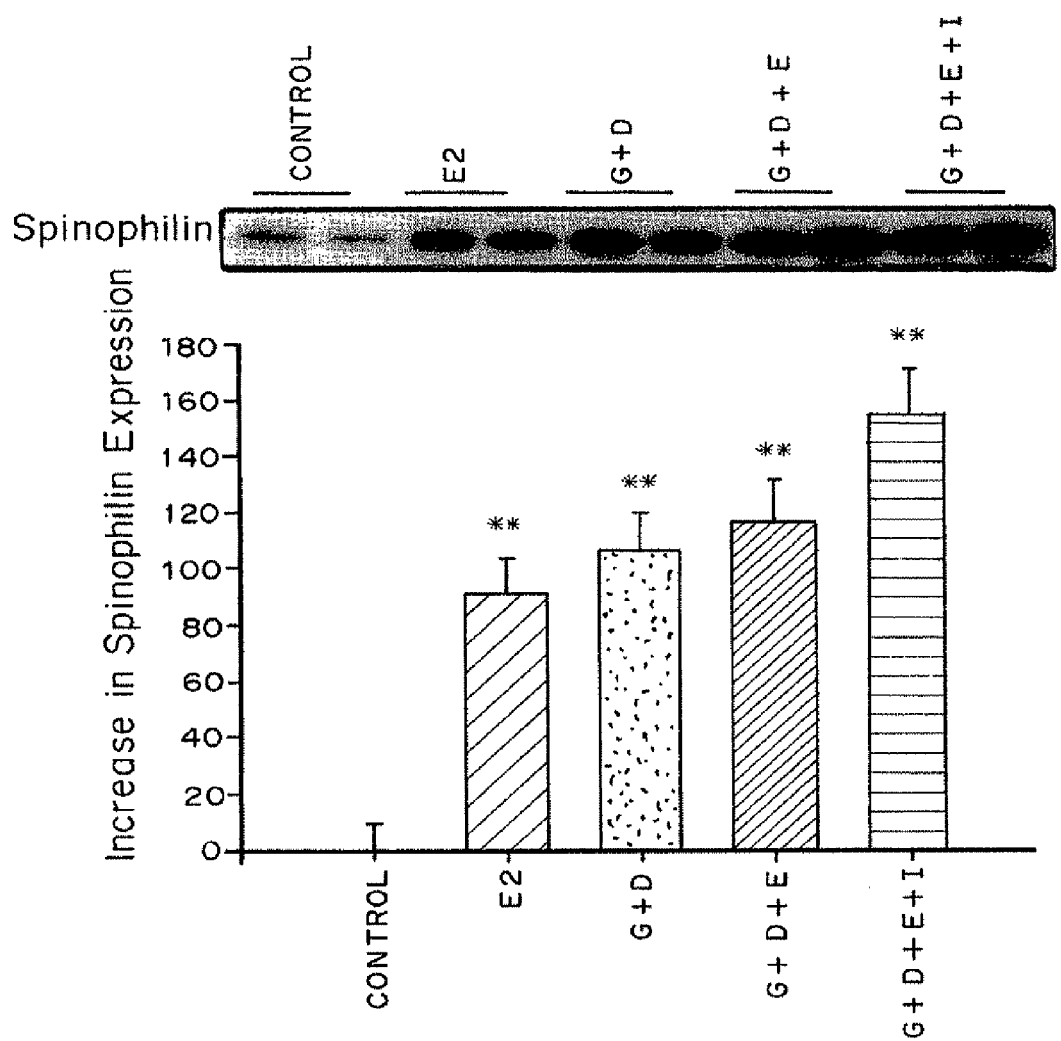
FIG. 6 is a graph illustrating the effect of four ERβ-selective phytoestrogenic molecules when co-administered (100 nM for all four molecules): G+D, G+D+E, or G+D+E+I, on the expression of the spine marker, spinophilin, in primary hippocampal neurons.
Figure 7A:
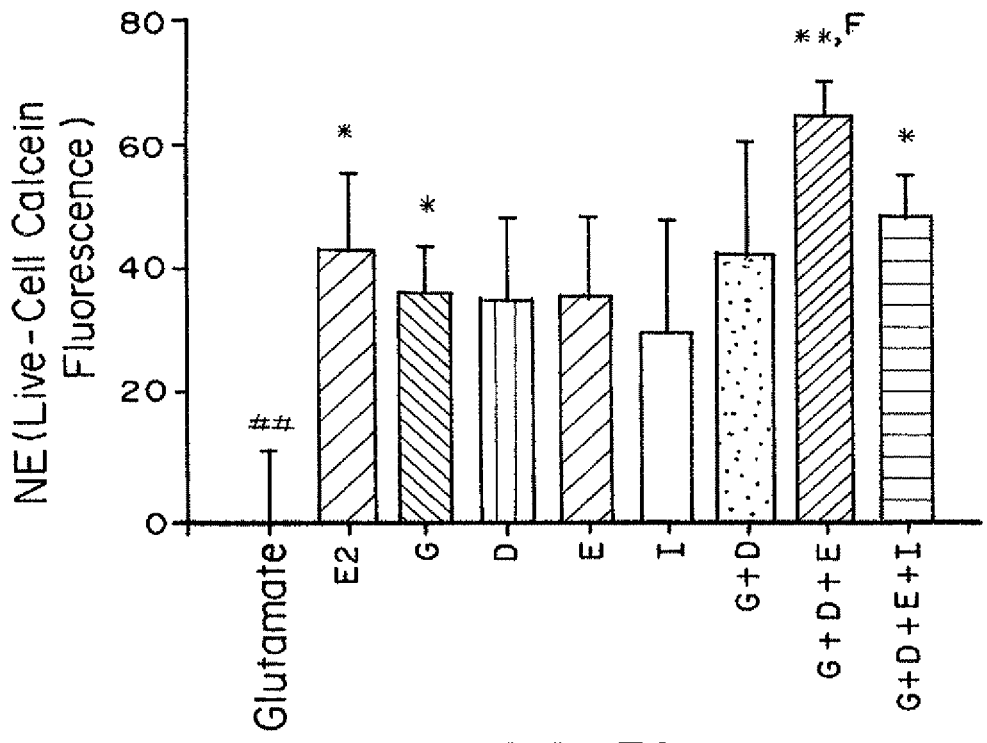
FIGS. 7A-7D are graphs shows the neuroprotective efficacy of G, D, E, and I, alone and in combination: G+D, G+D+E, or G+D+E+I, against (7A) glutamate- and (7B) β-amyloid1-42-induced neurotoxicity in rat primary hippocampal neurons, controls live/dead cells (7C); dead cells (7D).
Figure 7B:
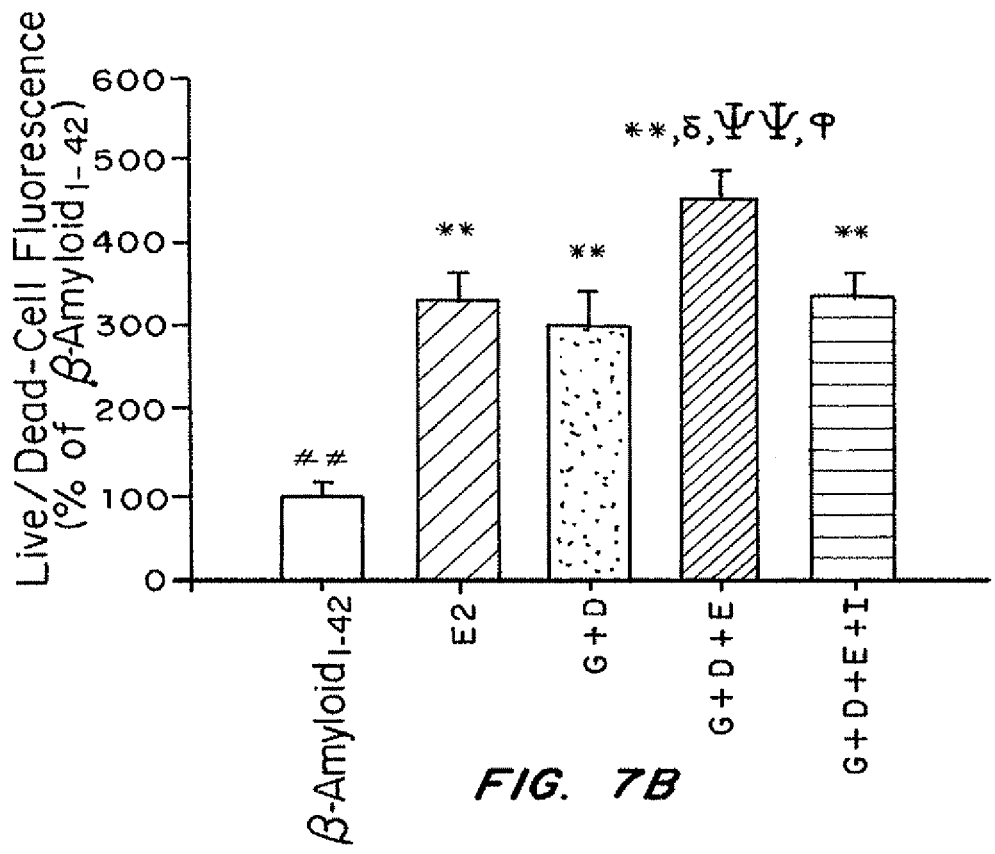
Figure 7C:
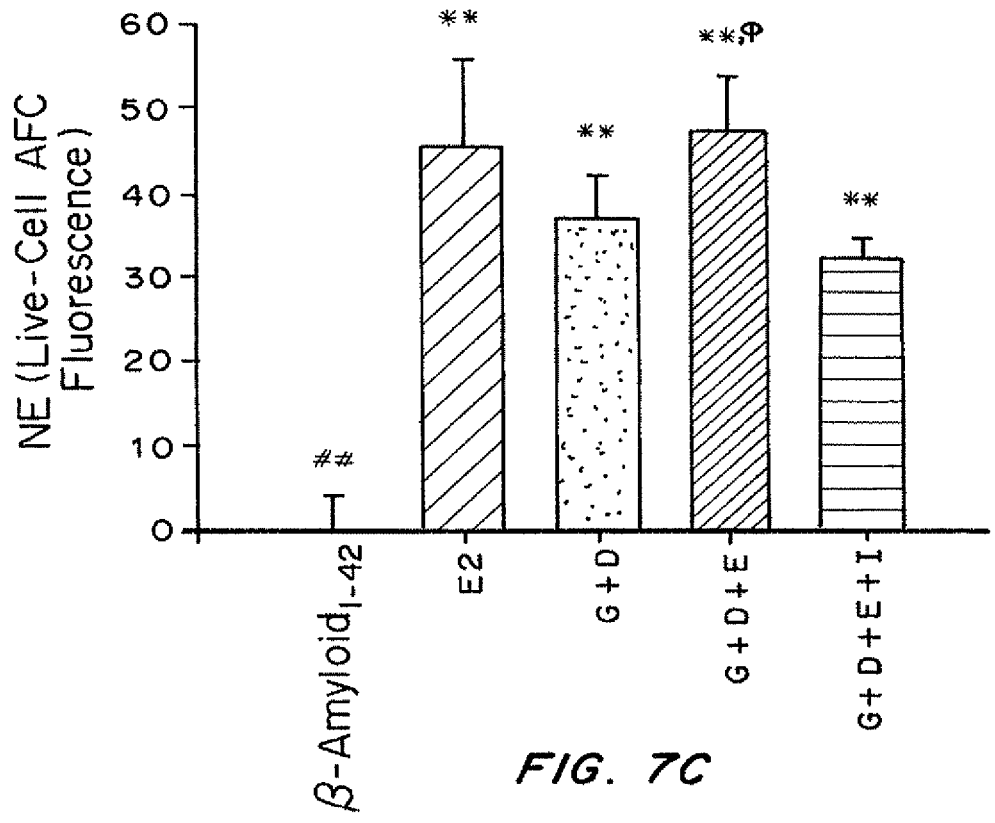
Figure 7D:
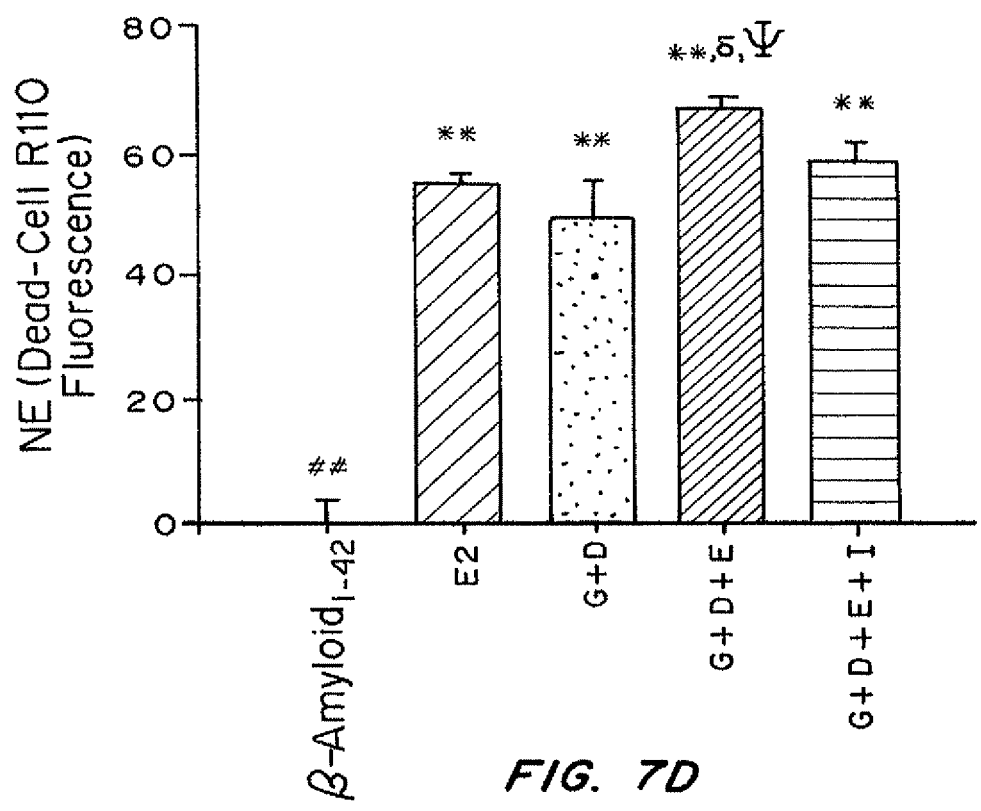

FIG. 6 illustrates the effect of four ERβ-selective phytoestrogenic molecules when co-administered (100 nM for all four molecules) on the expression of the spine marker, spinophilin, in primary hippocampal neurons. **P<0.01 compared to vehicle alone-treated cultures. Spinophilin, a protein that is enriched in the heads of neuronal dendritic spines, has been demonstrated to play a significant role in modulating both dendritic morphology and glutamatergic synaptic activity. Upregulation of spinophilin has been correlated with estrogen regulation of neuronal synaptic plasticity. Therefore, theses results indicate that these phytoestrogen combinations are effective to promote neurotrophism, thereby sustaining the brain staying in a synaptically active status, and prevent cognitive decline and memory loss.

Neuroprotection Against Glutamate

FIGS. 7A-7D shows the neuroprotective efficacy of the compounds against glutamate (FIG. 7A) and amyloid$_{1-42}$-induced neurotoxicity in rat primary hippocampal neurons. Primary hippocampal neurons grown for 7 divisions were pretreated with the test compounds (or combinations) for 48 h, followed by a 5-min exposure to 100 mM glutamate. Neurons were incubated for an additional 24 h prior to neuronal viability analyses by calcein AM staining. Following pretreatment with the compounds (or combinations) for 48 hr, neurons were exposed to 3 mM β-amyloid$_{1-42}$ for 2 d. Neuronal viability was analyzed by fluorometric measurements of activities of the LDH and dead-cell protease released in the culture media, and the live-cell protease exclusively entering intact viable neurons.

Results are presented as neuroprotective efficacy (NE), which is defined as the percentage of neurotoxin-induced toxicity prevented by the test compounds (or combinations) and quantitated by the equation:

$$NE=(V_{treatment}-V_{neurotoxin})/(V_{control}-V_{neurotoxin})*100\%$$

where $V_{treatment}$ is the individual value from the test compounds (or combinations)-treated cultures, $V_{neurotoxin}$ is a mean value from glutamate or β-amyloid$_{1-42}$ alone-treated cultures, and $V_{control}$ is a mean value from vehicle-treated control cultures. $^{\#\#}$P<0.01 compared to vehicle-treated control cultures; *P<0.05 and **P<0.01 compared to glutamate or β-amyloid$_{1-42}$ alone treated cultures; $^{\delta}$P<0.05 compared to E2-treated cultures; $^{\zeta}$P<0.05 compared to genistein-treated cultures; $^{\psi}$P<0.05 and $^{\psi\psi}$P<0.01 compared to combination (G+D)-treated cultures; $^{\Phi}$P<0.05 compared to combination (G+D+E+I)-treated cultures. Combined formulations were composed of equivalent molar of individual phytoSERMs included. G: genistein; D: daidzein; E: equol; I: IBSO03569.

Effect on IDE/NEP Expression

Figure 8A:
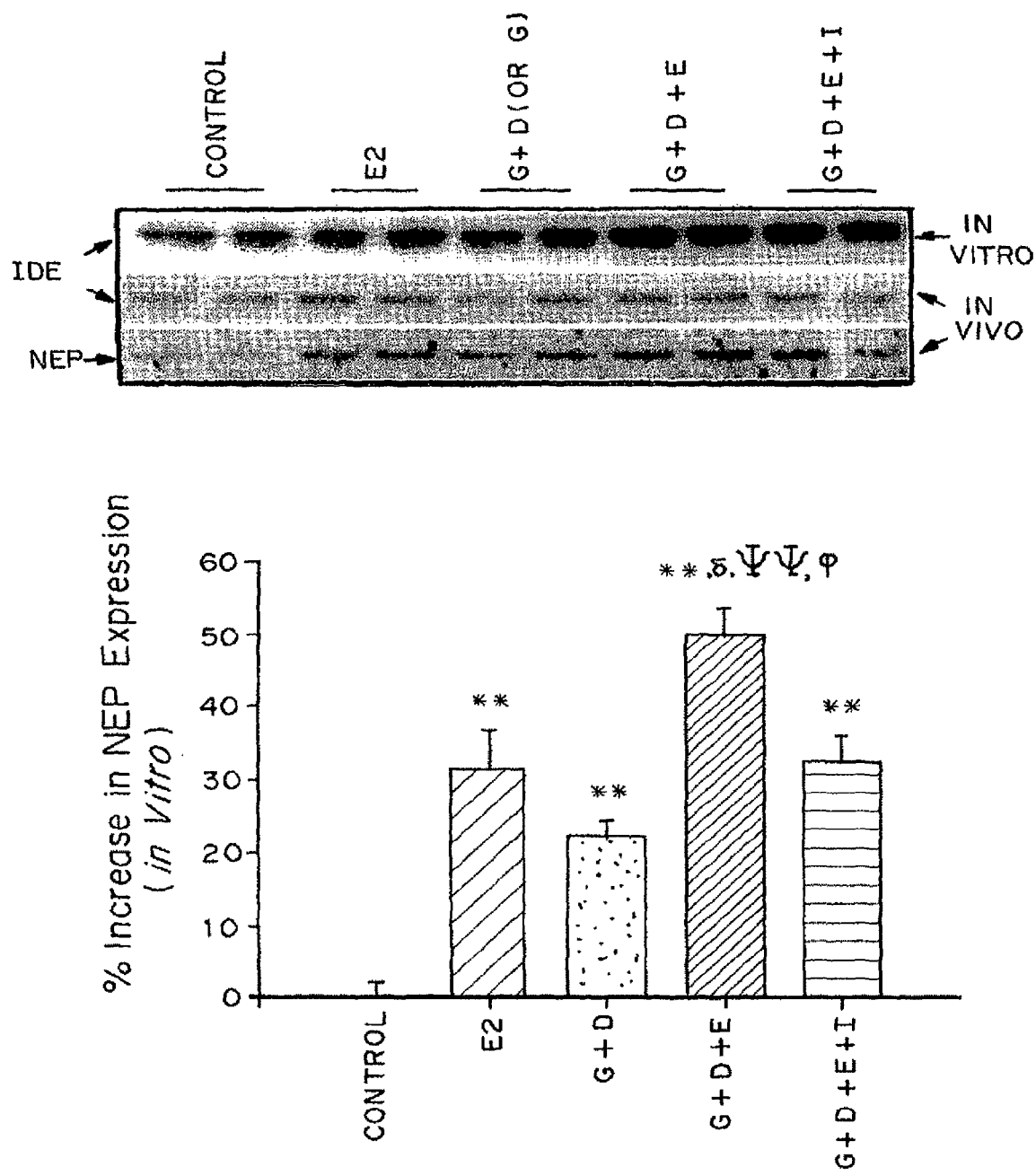
FIGS. 8A-8C are graphs showing the effects of G, D, E, and I, alone and in combination: G+D, G+D+E, and G+D+E+I, on insulin-degrading enzyme (IDE) expression on neprilysin (NEP) expression in hippocampal tissues derived from adult ovariectomized rats.
Figure 8B:
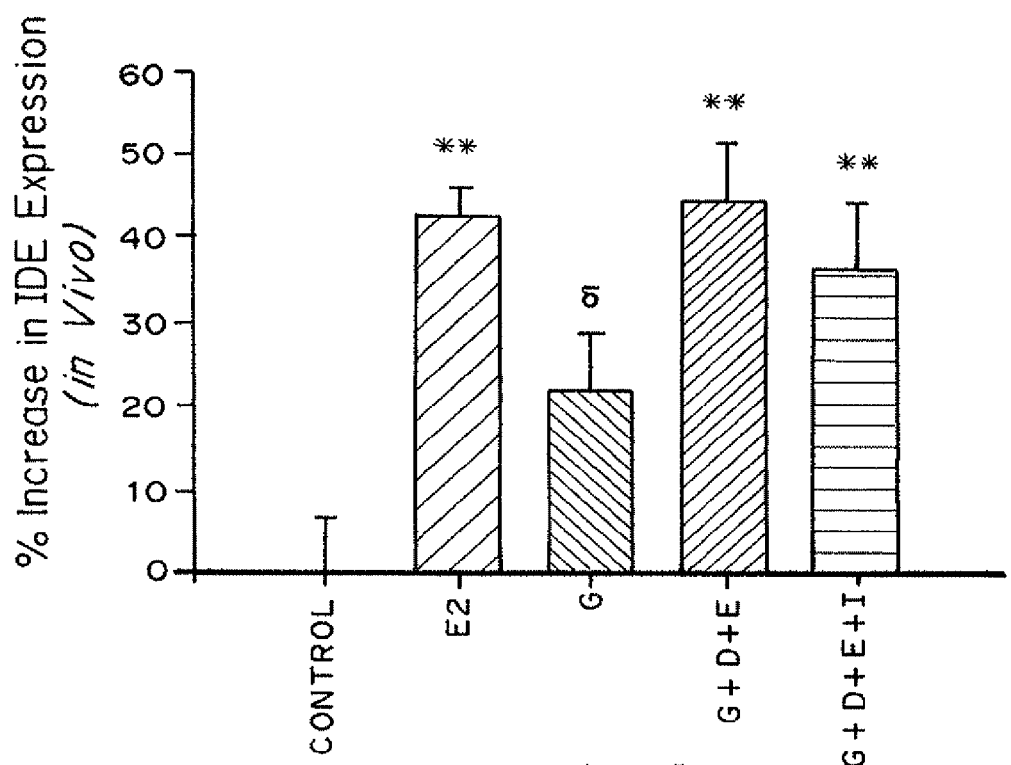
Figure 8C:
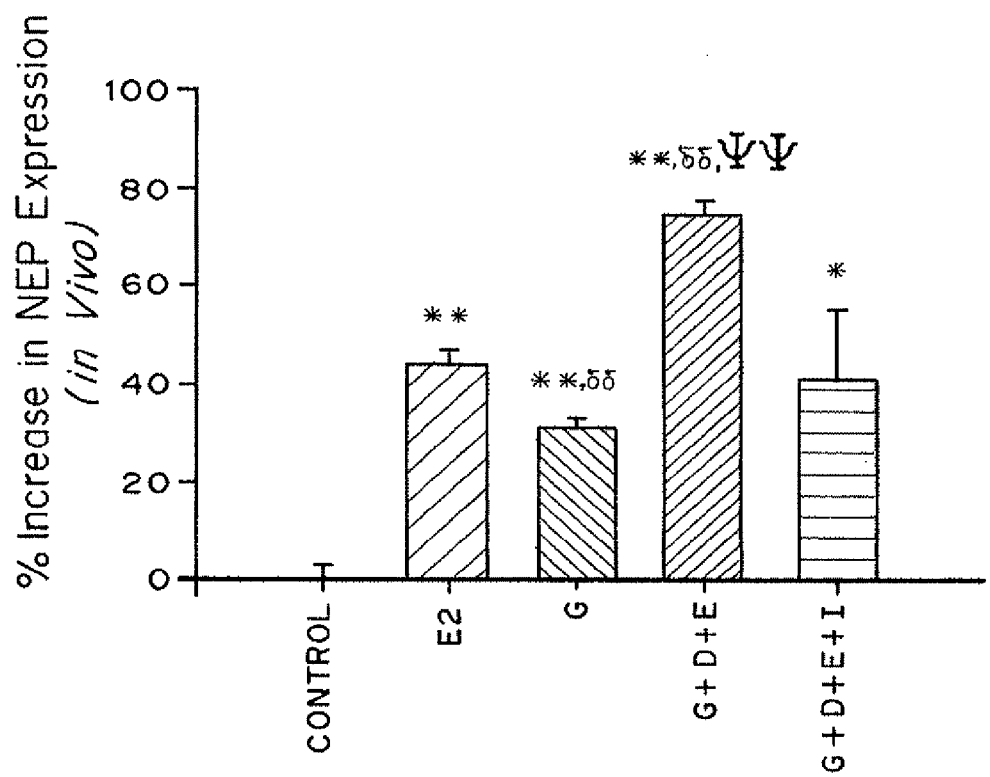
Figure 9A:
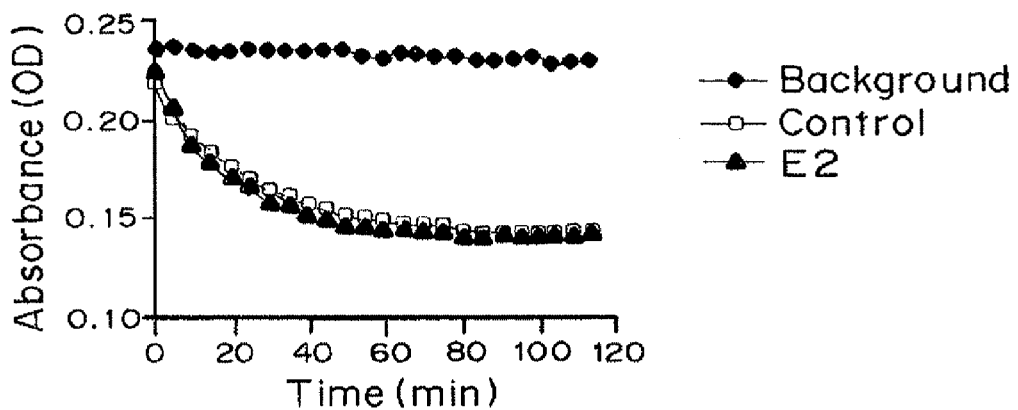
FIGS. 9A-9E are graphs showing the effects of G, G+D+E, and G+D+E+I on forebrain mitochondrial cytochrome c oxidase (COX) activity in adult ovariectomized rats.
Figure 9B:
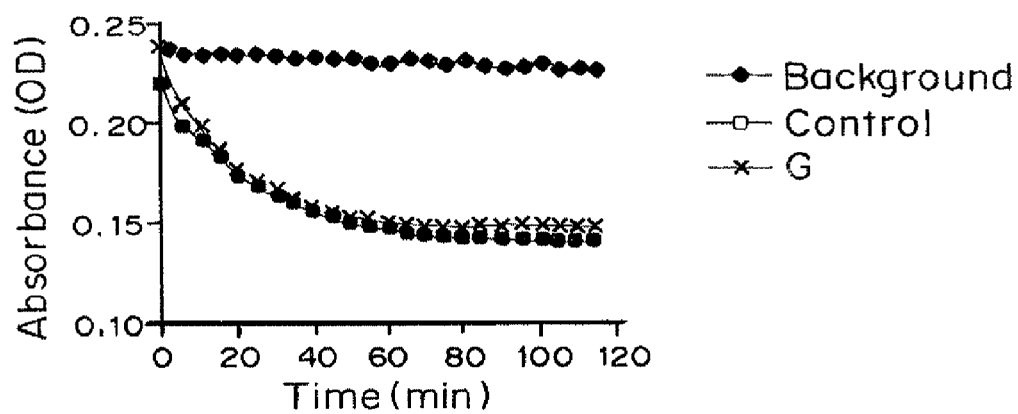
Figure 9C:
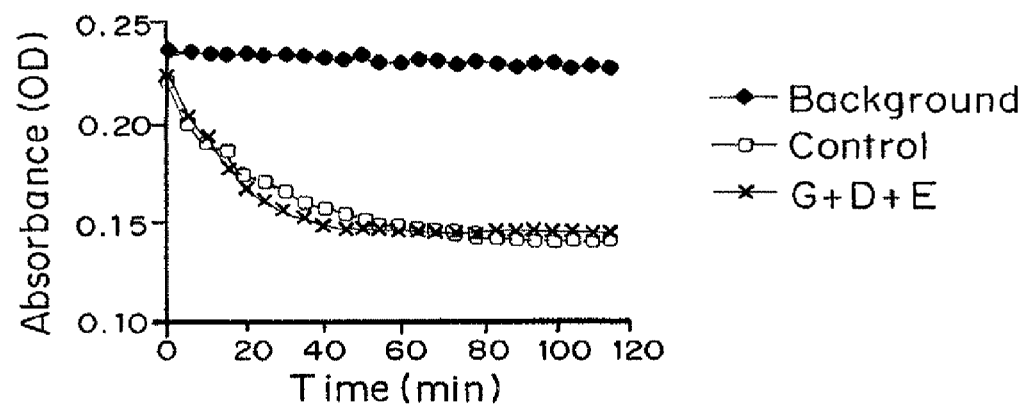
Figure 9D:
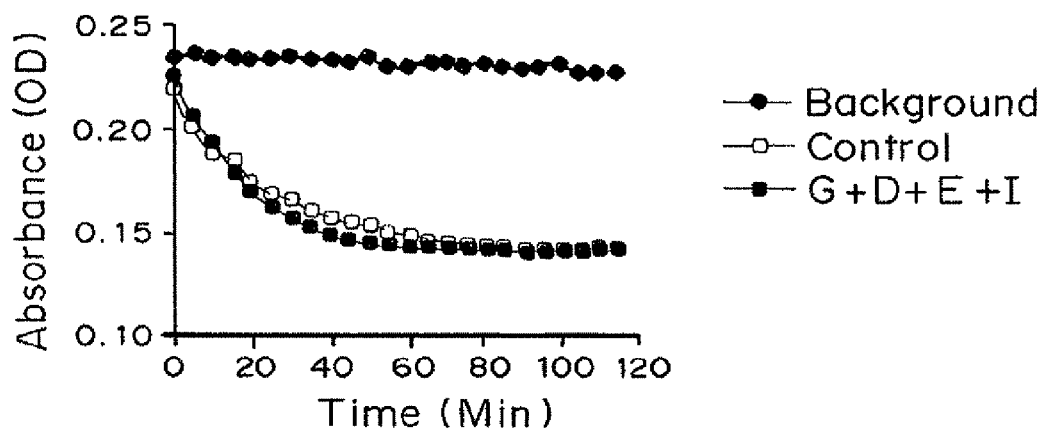
Figure 9E:
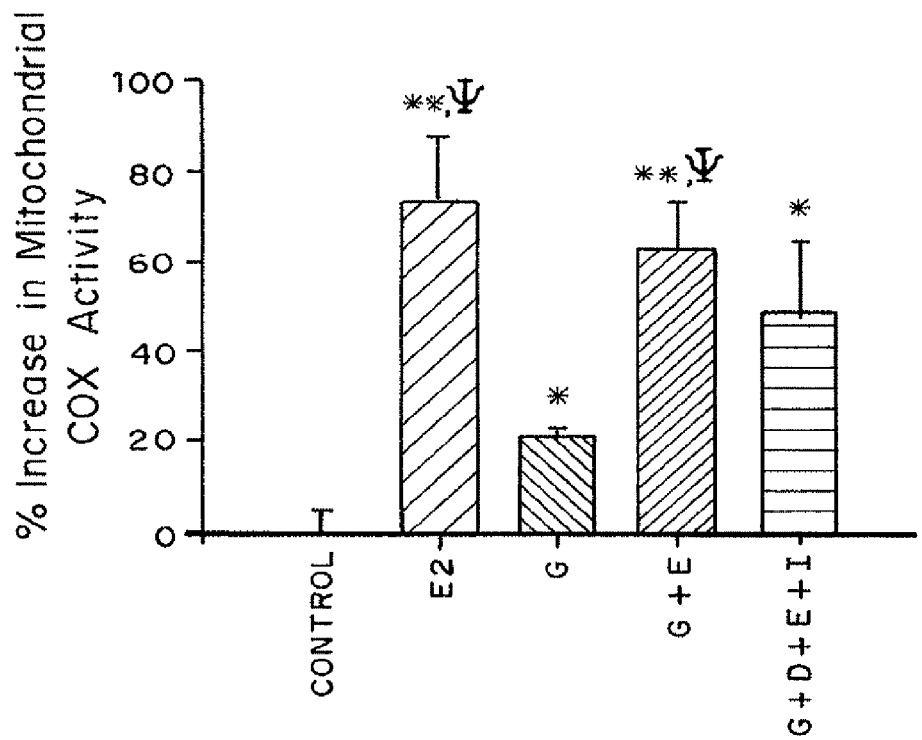
Figure 10A:
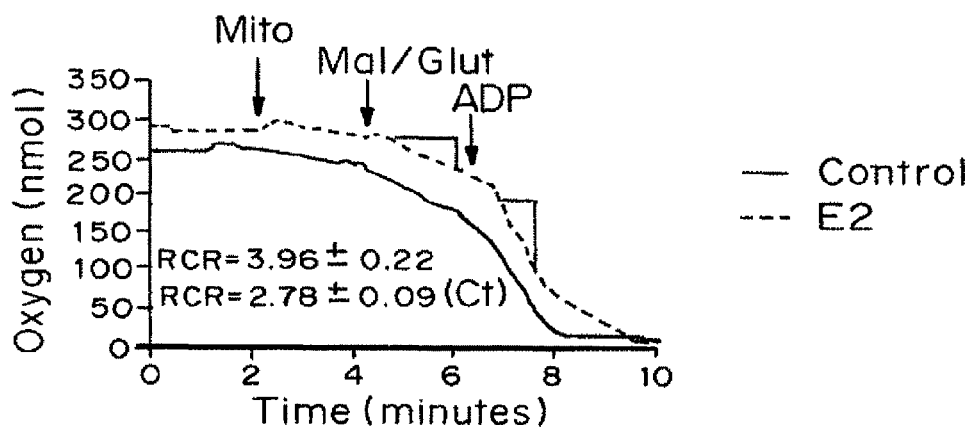
FIGS. 10A-10E are graphs showing the effects of G, G+D+E, and G+D+E+I on percent increase forebrain mitochondrial respiratory activity in adult ovariectomized rats.
Figure 10B:
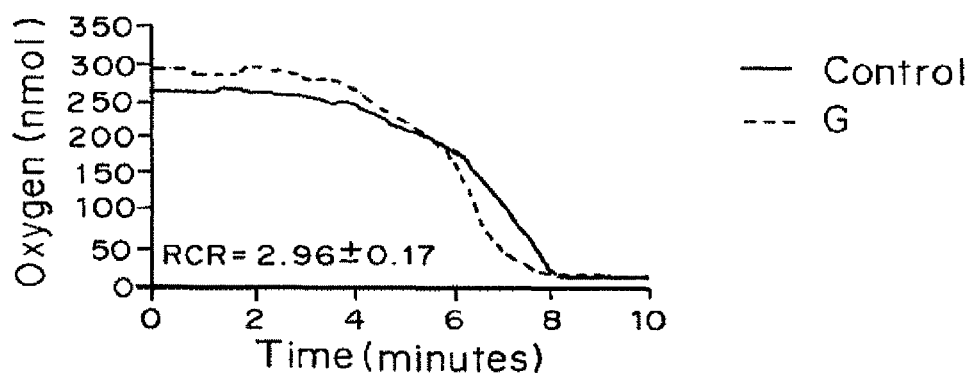
Figure 10C:
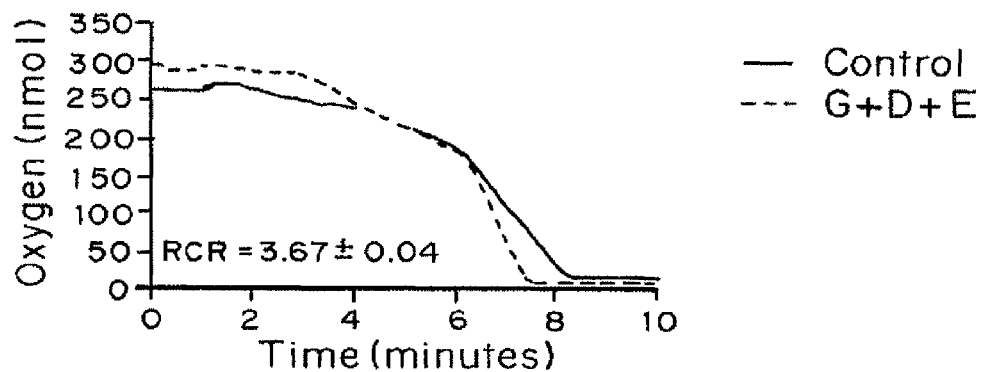
Figure 10D:
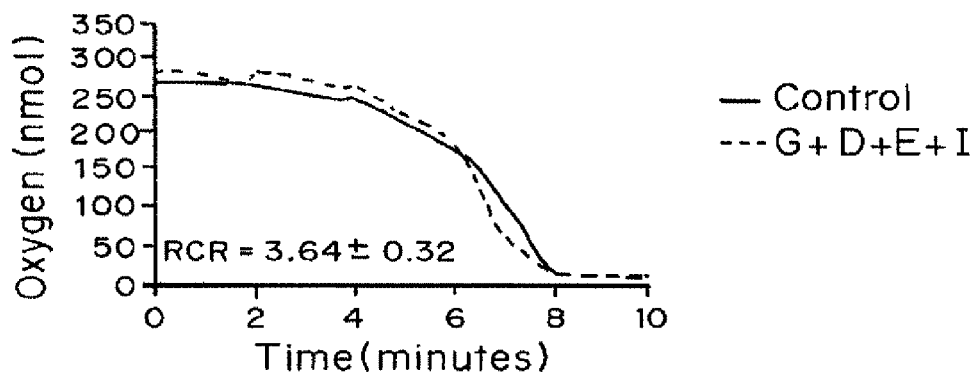
Figure 10E:
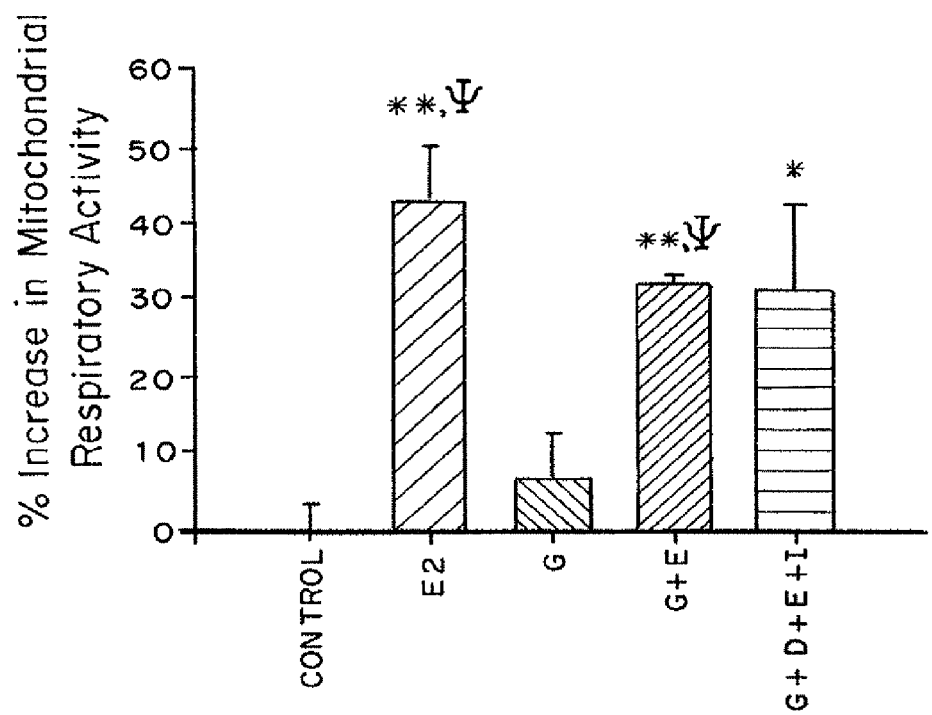

FIGS. 8A-8C show the effects on insulin-degrading enzyme (IDE)/neprilysin (NEP) expression in (A) rat primary hippocampal neurons and (B) hippocampal tissues derived from adult ovariectornized rats. (A) Primary hippocampal neurons grown for 7 DIV were treated with the test compounds (or combinations) for 48 hr followed by Western blot analyses. (B) Adult ovariectomized rats were given, once daily, 2 subcutaneous injections of the test compounds (or combinations). Rats were sacrificed 24 h later following the second injection. Hippocampal tissues were homogenized followed by western blot analyses. Results are presented as the fold increase in protein expression and expressed as the percent of control, n≥4. *P<0.05 and **P<0.01 compared to vehicle-treated control cultures or animals. $^\delta$P<0.05 and $^{\delta\delta}$P<0.01 compared to E2 treated cultures; $^{\psi\psi}$P<0.01 compared to combination (G+D) or genisteintreated cultures; $^\Phi$P<0.05 compared to combination (G+D+E+I)-treated cultures. Combined formulations were composed of equivalent molar in (A) and equivalent weight in (B) of individual phytoSERMs including G: genistein; D: daidzein; E: equal; and I: IBSO03569.

Effect on Forebrain Mitochondria

FIGS. 9A-9E show the effects on forebrain mitochondrial cytochrome c oxidase (COX) activity in adult ovariectomized rats. Rats were given, once daily, 2 subcutaneous injections of the test compounds (or combinations). Rats were sacrificed 24 h later following the 2nd injection. Forebrain mitochondria were isolated followed by a spectrophotometric measurement of COX activity using an immunocapture method. Colorimetric absorbance at 550 nm was recorded every 5 min for 115 min. COX activity is presented as the initial rate of oxidation of reduced cytochrome c, and determined by calculating the initial slope between two time points (<20 min) within the linear region. (Upper Panel) Time-lapse change in absorbance; (Lower Panel) % increase in mitochondria COX activity, n≥4; *P<0.05 and **P<0.01 compared to vehicle-treated control animals; $^\psi$P<0.05 compared to genistein-treated animals. Combined formulations were composed of equivalent weight of individual phytoSERMs including E2: 17bestradiol; G: genistein; D: daidzein; E: equal; I: IBSO03569.

FIGS. 10A-10E show the effects on forebrain mitochondrial respiratory activity in adult ovariectomized rats. Rats were treated as above. Forebrain mitochondria were isolated followed immediately by a polygraphical measurement of respiratory activity using an oxygen electrode. Following a basal recording, mitochondrial state 4 respiration was measured following the addition of substrates, malate/glutamate. State 3 respiration was measured following the addition of ADP. Respiratory control ratio (RCR) was calculated as the ratio between the rate of oxygen uptake at state 3 and the rate of oxygen uptake at state 4. (FIGS. 12A-12D) Time-lapse oxygen uptake; (FIG. 12E) % increase in mitochondrial respiratory activity, n≥4; *P<0.05 and **P<0.01 compared to vehicle-treated control animals; $^\psi$P<0.05 compared to genistein-treated animals. Combined formulations were composed of equivalent weight of individual phytoSERMs including E2: 17b-estradiol; G: genistein; D: daidzein; E: equol; and I: IBSO03569; Mito: mitochondria; Mal/Glut: malate/glutamate.

Effect on Uterine Weight

Table 4 shows the effects on uterine weight in adult ovariectomized rats. Changes in uterine weight in response to estrogenic stimulation can be used to evaluate the estrogenic characteristics of test compounds on uterine tissues. In one example, described below, immature female rats having low endogenous levels of estrogen are dosed with test compound (subcutaneously) daily for 3 days. Compounds are formulated as appropriate for subcutaneous injection. As a control, 17-β estradiol is administered alone to one dose group. Vehicle control dose groups are also included in the study. Twenty-four hours after the last treatment, the animals are necropsied, and their uteri excised, nicked, blotted and weighed. Any statistically significant increases in uterine weight in a particular dose group as compared to the vehicle control group demonstrate evidence of estrogenicity.

TABLE 4

Effects on uterine weight in adult ovariectomized rats[A]

| | Uterine Weight | | | |
|---|---|---|---|---|
| Treatment | Wet Weight (mg) | Increase (%)[B] | Dry Weight (mg) | Increase (%)[B] |
| Control (Vehicle) | 127.62 ± 10.75 | 0.00 ± 8.42 | 26.42 ± 2.45 | 0.00 ± 9.27 |
| 17β-Estradiol (70 μg/kg BW) | 281.06 ± 32.00**[D] | 120.23 ± 25.07**[D] | 46.70 ± 4.13**[D] | 76.74 ± 15.63**[D] |
| Genistein (6 mg/kg BW) | 144.11 ± 10.18 | 12.92 ± 7.97 | 28.14 ± 2.04 | 6.49 ± 7.71 |
| G + D + E (6 mg/kg BW)[C] | 119.84 ± 1.19 | −6.10 ± 0.93 | 23.71 ± 0.04 | −10.26 ± 0.13 |
| G + D + E + I (6 mg/kg BW)[C] | 146.99 ± 18.45 | 15.17 ± 14.46 | 28.73 ± 3.67 | 8.73 ± 13.90 |

[A]Adult ovariectomized rats were given, daily once, 2 subcutaneous injections of the test compounds (or combinations) (n ≥ 4 for each group). Rats were sacrificed 24 h later following the 2nd injection. Uteri were immediately excised and a wet weight was recorded. Uteri were then air dried for 1 hour followed by at 70° C. overnight, and the dry weight was recorded.
[B]Increase in uterine weight compared with vehicle-treated control animals and expressed as the percent of control (set as 0).
[C]Combined formulations were composed of equivalent weight of individual phytoSERMs included for a total amount of 6 mg/kg BW given to animals. G: genistein; D: daidzein; E: equol; I: IBSO03569.
[D]**P < 0.01 compared to any other treatment groups.

Summary

Both in vitro and in vivo analyses demonstrated that combined use of select test phytoSERMs provided significantly increased efficacy in sustaining neuronal survival when challenged with neurotoxins, promoting expression of proteins as key players in neuroprotection and metabolism/clearance of β-amyloid in neurons/brain, and enhancing brain mitochondrial functions. In particular, combined use of genistein, daidzein and equol at an equivalent weight afforded the maximal efficacy comparable or greater than 17b-estradiol in neuronal/brain assays. In contrast, such a combination showed no impact on uterine weight, which however was markedly increased by 17b-estradiol.

The present study indicates that combined use of select En-selective PhytoSERMs can be more therapeutically effective than single administrations and alternative combined formulations. In particular, the present study suggests the potential of the combination of genistein, daidzein and equol, at an equivalent weight, for prevention of neurodegeneration and AD, along with management of climacteric symptoms in postmenopausal women.

Figure 11A:
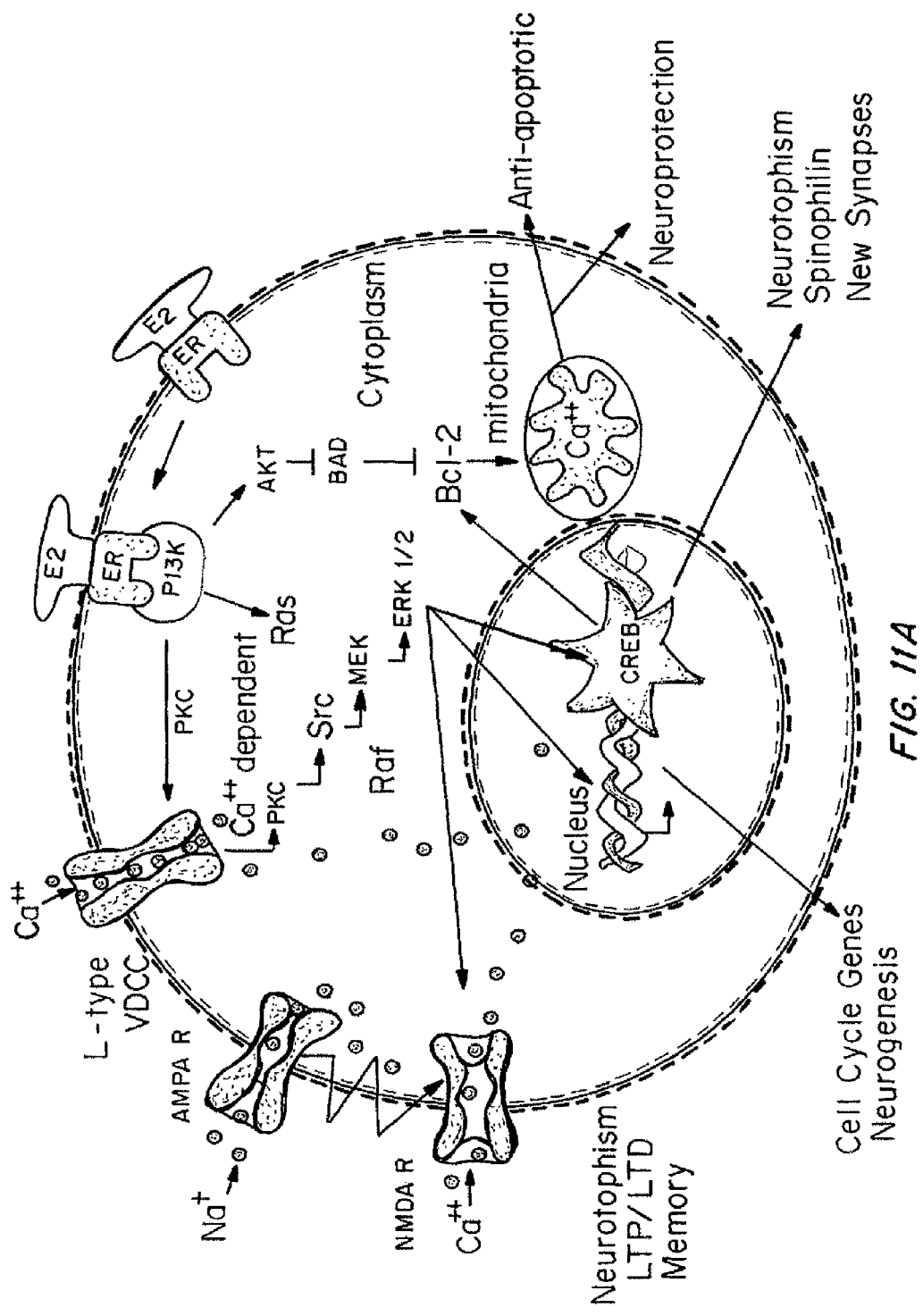
Figure 11C:
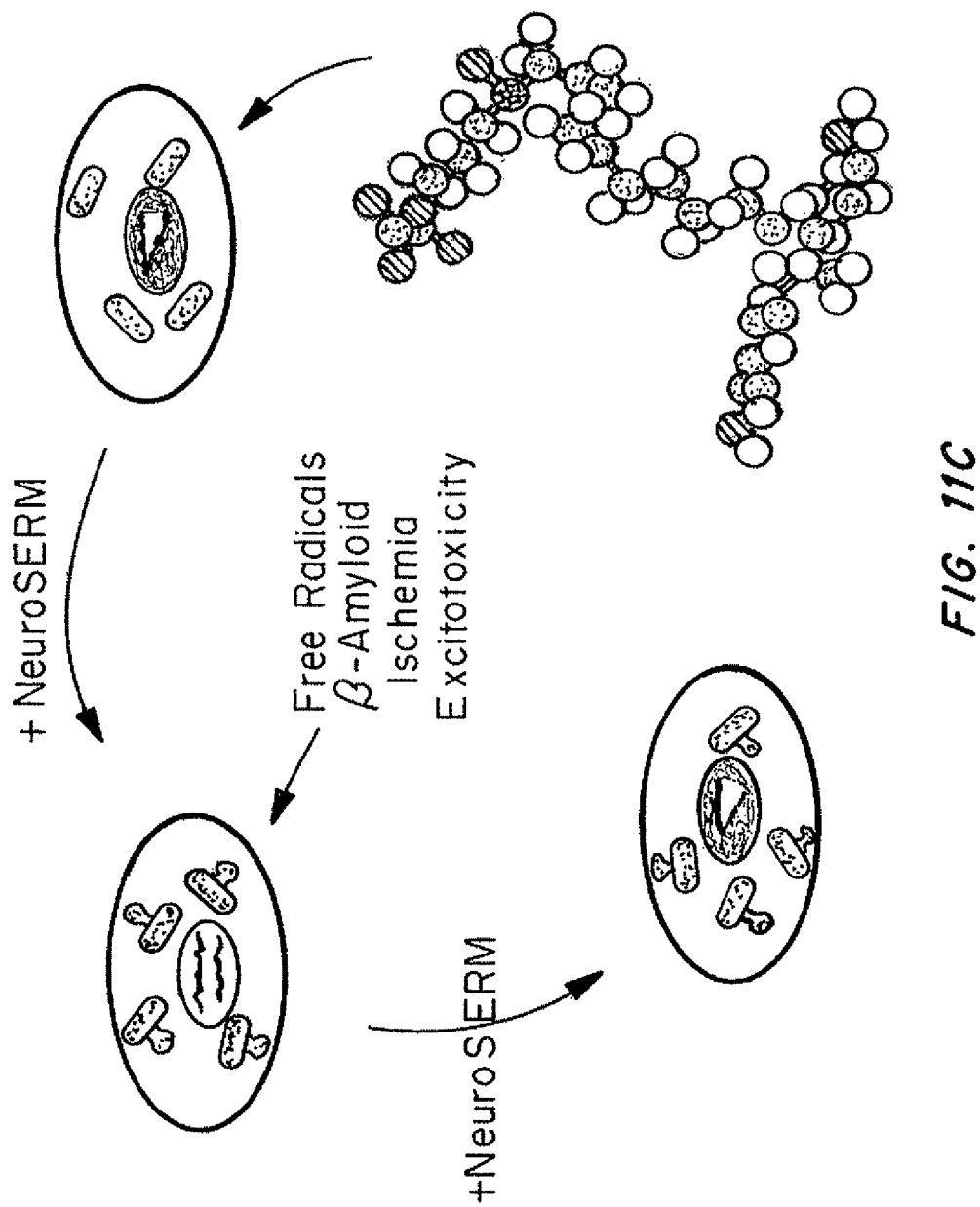

FIGS. 11A-11C are schematics showing estrogen mechanisms of action that lead to neurotrophic and neuroprotective outcomes. 17-β-Estradiol (E2) acting via a membrane-associated site (mER) activates a cascade required for multiple responses that lead to enhanced neural plasticity, morphogenesis, neurogenesis, and neural survival. The signaling sequence induced by E2 at the membrane site is as follows: (1) E2 binding to mER, (2) E2-mER complexes with p85 to activate PI3K, (3) activating calcium-independent PKC, (4) phosphorylating the L-type calcium channel, (5) inducing calcium influx, (6) activating calcium-dependent PKCs, (7) activating Src kinase, (8) activating the MEK/ERK1/2 pathway, (9) ERK translocates to the nucleus, (10) activating and phosphorylating CREB, (11) enhancing transcription of anti-apoptotic genes Bcl-2 and Bcl-xl, which enhance mitochondrial vitality, and spinophilin, which encourages synaptic growth, (12) simultaneously, estrogen activation of PI3K leads to activation of Akt, which phosphorylates and inhibits the proapoptotic protein BAD.

Estrogen-induced neuroprotective mechanisms converge on mitochondria. Estrogen-activated cellular signaling cascade promotes enhanced mitochondrial function, leading to increased calcium load tolerance, enhanced electron transport chain efficiency, and promotion of antioxidant defense mechanisms. These actions are mediated by the regulation of both nuclear and mitochondrial encoded genes initiated by the activation of second-messenger signaling cascades.

These mechanisms and the data herein demonstrate that, consistent with the healthy cell bias of estrogen benefit hypothesis, selective molecules can be administered before neurodegenerative insult while neurons are still healthy and that phytoSERM exposure will lead to enhanced neural survival mechanisms, represented as mitochondria with Bcl-2 additions, that promote neural defense against neurodegenerative insults associated with age-associated diseases such as Alzheimer's and Parkinson's.

These studies exemplify the therapeutic promise of select ERβ-selective phytoestrogens when used in combination for sustaining memory function and preventing age-related neurodegenerative insults and AD. These ERβ-selective phytoestrogen formulations, which optimize activation of ERβ while minimizing or avoiding activating ERα, should serve as an effective estrogen alternative replacement therapy for sustaining neurological health, function and prevention of AD without induction of proliferative responses in the reproductive tissues as seen with the current ET/HT. Moreover, in light of the most recent data indicating that activation of ERβ significantly reduces both ApoE mRNA and protein expression in neurons, ERβ-selective phytoestrogen formulations may serve as a particular viable strategy for reducing a major risk factor of AD in ApoE4 carriers.

We claimed:

1. A method for alleviating or preventing hot flashes in a patient comprising administering to the patient an effective amount of a formulation consisting of two or more phytoestrogen compounds or analogues thereof that selectively bind to estrogen receptor beta and cross the blood brain barrier, in a pharmaceutically acceptable excipient, wherein
    the patient is a menopausal or post-menopausal woman;
    the two or more phytoestrogen compounds are selected from the group consisting of genistein, daidzein, equol, IBSO03569, and combinations thereof, and are administered in an effective amount from about 1 mg/kg/day to about 10 mg/kg/day; and
    the phytoestrogen compounds are more effective in combination than the same amount of the individual phytoestrogen compounds.

2. The method of claim 1, wherein the phytoestrogen compounds are genistein and daidzein.

3. The method of claim 1, wherein one of the phytoestrogen compounds is equol.

4. The method of claim 3, wherein the phytoestrogen compounds are equol, genistein and daidzein.

5. The method of claim 3, wherein the phytoestrogen compounds are equol, genistein, daidzein and IBSO03569.

6. The method of claim 1, wherein the formulation is formulated for enteral, parenteral, or topical administration.

* * * * *

UNITED STATES PATENT AND TRADEMARK OFFICE
CERTIFICATE OF CORRECTION

PATENT NO. : 8,552,057 B2  Page 1 of 2
APPLICATION NO. : 13/362825
DATED : October 8, 2013
INVENTOR(S) : Roberta Diaz Brinton and Liqin Zhao It is certified that error appears in the above-identified patent and that said Letters Patent is hereby corrected as shown below:

In the Drawings

Sheet 1, FIG. 1, replace the structure of 17β-Estradiol " 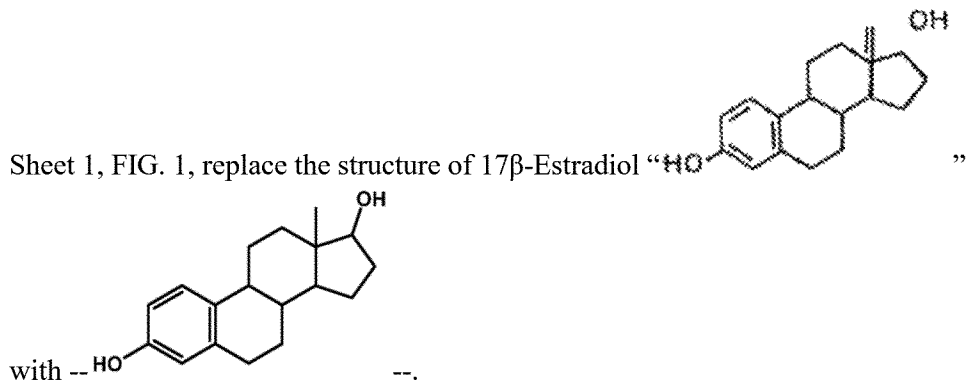 " with -- --.

Sheet 1, FIG. 1, replace the structure of Equol " 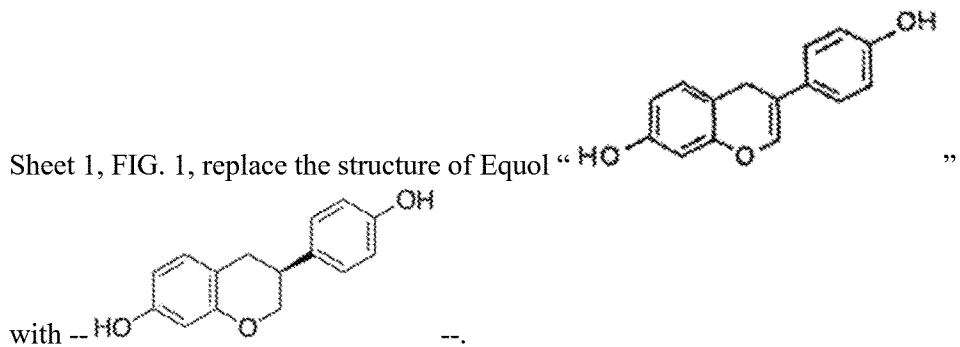 " with -- --.

Signed and Sealed this
Third Day of November, 2020

Andrei Iancu
*Director of the United States Patent and Trademark Office*

In the Specification
Column 17, compound 2, replace the structure " 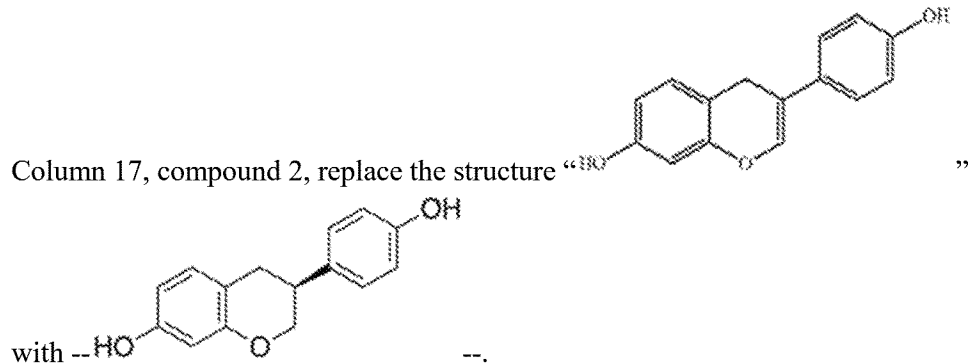 "
with -- -- .
In the Claims
Claim 1, Column 34, Line 22, replace "equol" with --(S)-equol--.
Claim 3, Column 34, Line 32, replace "equol" with --(S)-equol--.
Claim 4, Column 34, Line 34, replace "equol" with --(S)-equol--.
Claim 5, Column 34, Line 36, replace "equol" with --(S)-equol--.